(12) United States Patent
Lee et al.

(10) Patent No.: US 9,345,789 B2
(45) Date of Patent: May 24, 2016

(54) SPECIFIC INHIBITORS AND ACTIVE SITE PROBES FOR LEGUMAIN

(75) Inventors: Jiyoun Lee, Stanford, CA (US);
Fangfang Yin, Stanford, CA (US);
Matthew S. Bogyo, Redwood City, CA (US); Laura E. Edgington, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 785 days.

(21) Appl. No.: 13/516,643

(22) PCT Filed: Dec. 17, 2010

(86) PCT No.: PCT/US2010/061109
§ 371 (c)(1),
(2), (4) Date: Jun. 15, 2012

(87) PCT Pub. No.: WO2011/075678
PCT Pub. Date: Jun. 23, 2011

(65) Prior Publication Data
US 2012/0251459 A1    Oct. 4, 2012

Related U.S. Application Data

(60) Provisional application No. 61/287,976, filed on Dec. 18, 2009.

(51) Int. Cl.
| | |
|---|---|
| *A61K 51/00* | (2006.01) |
| *A61M 36/14* | (2006.01) |
| *A61K 49/00* | (2006.01) |
| *C07K 5/065* | (2006.01) |
| *C07K 5/068* | (2006.01) |
| *C07K 5/078* | (2006.01) |

(52) U.S. Cl.
CPC ......... *A61K 49/0056* (2013.01); *A61K 49/0032* (2013.01); *A61K 49/0052* (2013.01); *C07K 5/06078* (2013.01); *C07K 5/06086* (2013.01); *C07K 5/06139* (2013.01)

(58) Field of Classification Search
CPC ..... A61K 49/00; A61K 38/00; A61K 38/005; A61K 38/02; A61K 38/03; A61K 38/04; A61K 38/17; A61K 49/0032; A61K 49/0052; A61K 49/10; A61K 49/12; A61K 49/14; A61K 51/00; A61K 51/08; A61K 51/088; C07K 5/06139; C07K 5/06078; C07K 5/06086
USPC ........... 424/1.11, 1.37, 1.65, 1.69, 1.81, 1.85, 424/1.89, 9.1, 9.2, 9.3, 9.4, 9.5, 9.6; 514/1, 514/1.1
See application file for complete search history.

(56) References Cited

U.S. PATENT DOCUMENTS

| | | |
|---|---|---|
| 4,444,690 A | 4/1984 | Fritzberg |
| 4,479,930 A | 10/1984 | Hnatowich |
| 4,861,869 A | 8/1989 | Nicolotti et al. |
| 4,965,392 A | 10/1990 | Fritzberg et al. |
| 5,120,526 A | 6/1992 | Fritzberg et al. |
| 5,175,257 A | 12/1992 | Kasina et al. |
| 5,310,536 A | 5/1994 | Srinivasan |
| 5,830,431 A | 11/1998 | Srinivasan et al. |
| 6,323,313 B1 | 11/2001 | Tait et al. |
| 6,589,503 B1 | 7/2003 | Piwnica-Worms |
| 7,056,947 B2 | 6/2006 | Powers et al. |
| 2007/0036725 A1 | 2/2007 | Bogyo et al. |
| 2008/0176841 A1 | 7/2008 | Bogyo et al. |
| 2009/0252677 A1 | 10/2009 | Bogyo et al. |
| 2010/0003735 A1 | 1/2010 | Bogyo et al. |
| 2010/0068150 A1 | 3/2010 | Bogyo et al. |
| 2012/0251459 A1 | 10/2012 | Lee et al. |

OTHER PUBLICATIONS

Lee et al (ACS Chemical Biology, Published online on Dec. 17, 2009, vol. 5, No. 2, pp. 235-243).*
ISR and WO, PCT/US10/61109, Apr. 27, 2011.
Lee et al., "Development of near-infrared fluorophore (NIRF)-labeled activity-based probes for in vivo imaging of legumain", Chemical Biology, Dec. 17, 2009, 5(2):233-243.
Gotz, et al., "Aza-peptidyl Michael acceptors. A new class of potent and selective inhibitors of asparaginyl endopeptidases (legumains) from evolutionarily diverse pathogens", Journal of Medicinal Chemistry 2008, 51, No. 9: 2816-2832.
Greenbaum et al., "Small Molecule Affinity Fingerprinting: a Tool for Enzyme Family Subclassification, Target Identification, and Inhibitor Design", Chemistry and Biology, vol. 9, 1085-1094, Oct. 2002.
James, et al., "Aza-peptide epoxides: potent and selective inhibitors of schistosoma mansoni and pig kidney legumains (asparaginyl endopeptidases)", Biol. Chem., vol. 384, pp. 1613-1618, Dec. 2003.
Gotz "Design, synthesis, and evaluation of irreversible peptidyl inhibitors for clan ca and clan cd cysteine proteases", Dissertation, Georgia Institute of Technology, May 2004.
Sexton, et al., "Specificity of aza-peptide electrophile activity-based probes of caspases", Cell and Death Differentiation, 2007, 14, 727-732.

* cited by examiner

*Primary Examiner* — D L Jones
(74) *Attorney, Agent, or Firm* — Bozicevic, Field & Francis LLP

(57) ABSTRACT

Compounds which specifically inhibit legumain, also known as asparaginyl endopeptidase are provided. The compounds have an epoxide or N-Michael acceptor warhead, and have an asparagine side chain attached to a nitrogen atom in the backbone adjacent the warhead. The compounds also preferably comprise a proline residue adjacent the asparagine, and the compound may also contain a third residue and/or a label for cellular or in vivo imaging of active legumain.

22 Claims, 22 Drawing Sheets

(Control)

Legumain probe 2

Legumain inhibitor 2

LI-1
(Legumain inhibitor -1)

Control LI-0
(Legumain inhibitor -0)

| | Legumain | | Cathepsin B | Cathepsin L | Caspase-3 |
|---|---|---|---|---|---|
| Inhibitor | IC$_{50}$ | k$_{obs}$/[I] | IC$_{50}$ | IC$_{50}$ | IC$_{50}$ |
| LI-0 | 704 nM | 1586 M$^{-1}$s$^{-1}$ | > 1 mM | > 1 mM | 2.8 μM |
| LI-1 | 11.5 nM | 72252 M$^{-1}$s$^{-1}$ | 390 μM | 220 μM | 890 μM |
| LI-2 | 145 nM | 10802 M$^{-1}$s$^{-1}$ | > 1mM | N/D | N/D |
| JPM-OEt[a] | N/D | | 0.78 μM | 2.7 μM | |
| Z-DEVD-FMK[b] | N/D | | N/D | N/D | 0.13 μM |

SPECIFIC INHIBITORS AND ACTIVE SITE PROBES FOR LEGUMAIN

CROSS-REFERENCE TO RELATED APPLICATIONS

This application claims priority to U.S. provisional Application No. 61/287,976 filed on Dec. 18, 2009, hereby incorporated by reference, and this application further claims priority as the national stage of PCT/US2010/061109, having an international filing date of 17 Dec. 2010, which is hereby incorporated by reference in its entirety.

STATEMENT OF GOVERNMENTAL SUPPORT

This invention was made with Government support under contract R01-EB005011 awarded by the National Institutes of Health. The Government has certain rights in the invention.

REFERENCE TO SEQUENCE LISTING, COMPUTER PROGRAM, OR COMPACT DISK

The instant application contains a Sequence Listing which has been submitted as an ASCII text file and is hereby incorporated by reference in its entirety. This text file was created on Jun. 15, 2012, is named "3815_77_1_Seq_List.txt" and is 4096 bytes in size.

BACKGROUND OF THE INVENTION

1. Field of the Invention

The present invention relates to the field of organic compounds and to methods for specifically binding and labeling enzymes, particularly cysteine proteases, and more particularly legumain, also known as asparaginyl endopeptidase. The present compounds may be labeled for use in imaging and are designed to chemically attach to the active site of the target enzyme.

2. Related Art

Presented below is background information on certain aspects of the present invention as they may relate to technical features referred to in the detailed description, but not necessarily described in detail. That is, individual structures or methods used in the present invention may be described in greater detail in the materials cited below, which materials may provide further guidance to those skilled in the art for making or using certain aspects of the present invention as claimed. The discussion below should not be construed as an admission as to the relevance of the information to any claims herein or the prior art effect of the material described.

Cysteine proteases are proteolytic enzymes, which utilize a cysteine residue for their catalytic activity. They can be grouped into at least 30 protein families. Each family contains proteins with similar amino acid sequences and evolutionarily conserved sequence motifs, which are reflected in the family members' similar 3D structures.

Proteases in Family C1 (the papain family) include mammalian enzymes such as cathepsins B and L, which are thought to be involved in cancer growth and metastasis. Cathepsin K is considered to be involved in bone degradation an osteoporosis. Family C1 also includes parasitic enzymes being essential for the parasite-host interaction (e.g., cruzipain from *Trypanosoma cruzi*—causing Chagas' disease, and falcipain from *Plasmodium falciparum*—causing malaria). Enzymes belonging to Family C13 (the legumain family) have been shown to play key roles in antigen presentation.

Asparaginyl endopeptidase, or legumain (Enzyme Class 3.4.22.34), is a lysosomal cysteine protease that was originally identified in plants and later found to be involved in antigen presentation in higher eukaryotes. Legumain is also up-regulated in a number of human cancers and recent studies suggest that it may play important functional roles in the process of tumorigenesis. However, detailed functional studies in relevant animal models of human disease have been hindered by the lack of suitably selective small molecule inhibitors and imaging reagents.

Legumain is a lysosomal cysteine protease that was named based on its propensity to cleave protein substrates on the C-terminal side of asparagine residues (1). Legumain is expressed in diverse cell types, and in most cases, its functions are unknown. Recently legumain has emerged as an important enzyme in antigen processing (2, 3) and matrix degradation (4, 5) and it is implicated in various pathological conditions including parasite infection (6, 7), atherosclerosis (8) and tumorigenesis (9, 10). For example, legumain is heavily over-expressed in the majority of human solid tumors such as carcinomas of the breast, colon and prostate (9). Furthermore, knock-down of legumain in mouse models of cancer resulted in a marked decrease in tumor growth and metastasis (10). More recently, mice lacking legumain develop disorders similar to hemophagocytic syndrome, a form of hyperinflammatory response (11). Despite the mounting evidence of legumain as a therapeutically important target, especially in tumor progression and metastasis, current methods to study legumain function mainly depend on antibodies and genetic modification, making it difficult to study legumain in its native state.

Small molecule chemical tools such as activity-based probes (ABPs) provide a highly versatile means to monitor protease function and regulation in a wide range of biological systems. Typical ABPs utilize irreversible inhibitors that can covalently modify active site of enzyme in an activity dependent fashion. However, only a few legumain-specific inhibitors have appeared in the literature thus far. All of these inhibitors have a Cbz-Ala-Ala-Asn peptide scaffold that is based on the sequence of a known substrate of legumain (12). In addition, a number of different reactive electrophilic functional groups including aza-Asn halomethylketones (13), aza-Asn epoxides (7) and aza-Asn Michael acceptors (6) have been used to make irreversible legumain inhibitors. Although these inhibitors are highly potent against legumain in vitro, their potency, and more importantly, their selectivity in vivo, has never been tested. We have previously developed a cell-permeable ABP for legumain that is composed of a peptide acyloxymethyl ketone (AOMK) with a PI aspartic acid (14). Although this probe is useful to study active legumain in cells, it has overall poor potency and can readily cross react with caspases, which also optimally bind to aspartic acid containing AOMKs (15). In view of various shortcomings of prior art legumain inhibitors, we decided to create a new class of legumain inhibitors with faster kinetic properties and increased selectivity for legumain for use in vivo imaging studies. We found, among other things, that the new probes described here (LP-1 in particular are) extremely selective toward legumain and exhibit almost no cross-reactivity towards any other enzymes, even in vivo. The results below demonstrate that one sees only labeled legumain in extracts from whole tissues upon administration of the present probes in vivo.

Described below is a new class of aza-Asn ABPs for legumain that are labeled with Cy5 fluorophore, or other label useful for imaging, and also may be tagged with a series of cell-permeabilizing groups. This new generation of legumain probes can have either an epoxide or Michael acceptor warhead and may be used to image active legumain in vivo both in normal tissues and within solid tumors.

Specific Patents and Publications

Epoxides have been used in cysteine protease inhibitors previously. The general epoxide scaffold for JPM-OEt is based on E-64, which was discovered to be a natural product inhibitor of a variety of cysteine protease in 1978 (Hanada, K. et al. Agric. Biol. Chem. 1978 42, 523-528 and 529-536).

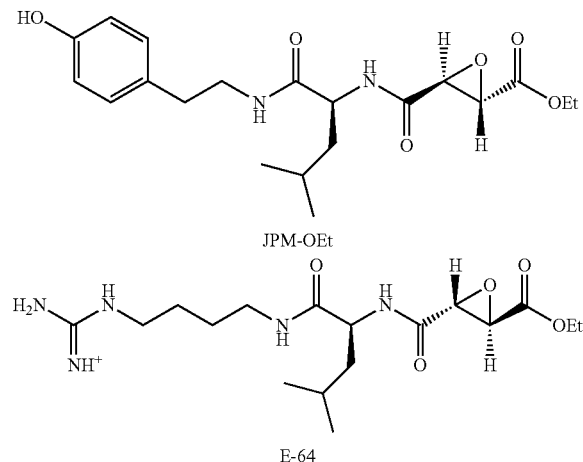

JPM-OEt

E-64

A related compound, JPM-565, is identical to JPM-OEt except that the ethyl ester is converted to the free carboxylic acid.

These classes of compounds have been used as cysteine protease inhibitors since 1978. A number of research groups have synthesized analogs of the general epoxide structure over the past 20+ years and the crystal structure of E-64 bound to various cysteine proteases in the cathepsin family were reported as early as 1989.

Greenbaum et al. *Chem. Biol.* 2002, 9, 1085-1094 also describe cysteine protease inhibitors that target the same subset of proteases targeted by E-64 and JPM-565. It is noted there that the epoxide class of cysteine protease binding compounds has a chiral structure, e.g., as shown. The following general inhibitor is disclosed:

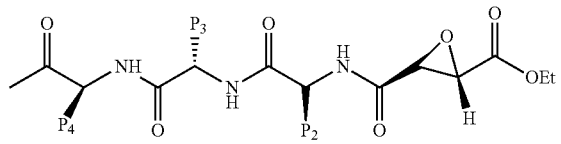

Libraries of different amino acids substituted for P2, P3, and P4 were prepared. The libraries were first prepared by fixing each of the P2, P3, and P4 positions with each of the 20 possible natural amino acids (minus cysteine and methionine, plus norleucine).

It should be noted that these structures do not utilize N—N bonds or N-linked side chains.

BRIEF SUMMARY OF THE INVENTION

The following brief summary is not intended to include all features and aspects of the present invention, nor does it imply that the invention must include all features and aspects discussed in this summary.

The present invention relates to a series of compounds illustrated by the general Formula of Formula I, and illustrated by inhibitors or probes LI/P-1, LI/P-2 and LI/P-3:

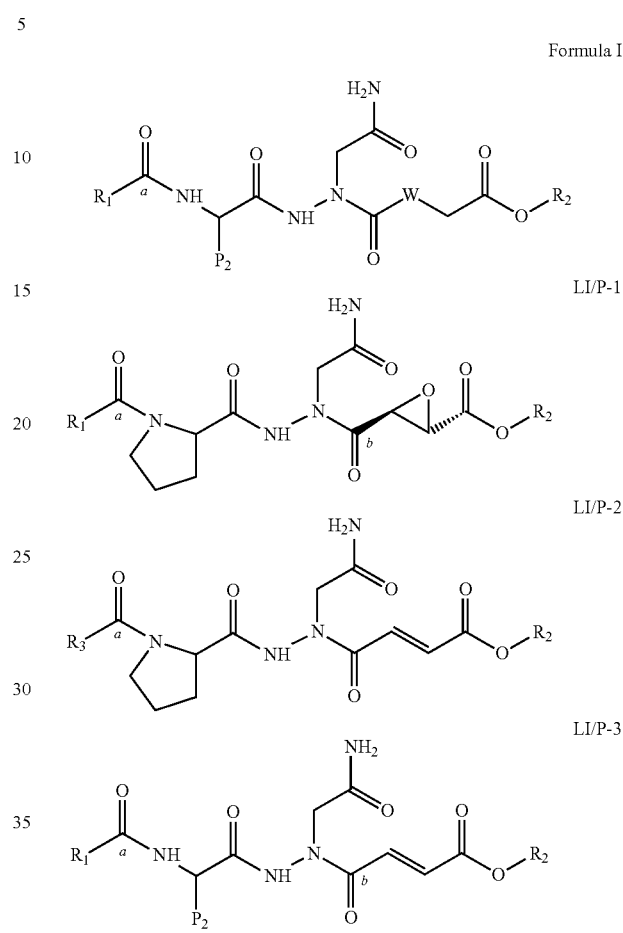

In Formula I above, W represents a warhead, which is either epoxide, i.e.,

or a Michael acceptor, e.g. an ethylenyl group, —C=C— as contained in the above structure. An epoxide warhead is illustrated in LI/P-1 and an N-Michael acceptor is illustrated in LI/P-2 and LI/P-3. An exemplary succinyl epoxide (LI/P-1) warhead has the formula: —$C_1$—O—$C_2$—C(=O)—O—, where $C_1$ and $C_2$ are also bonded together to form an epoxide ring.

R1 is selected from the group consisting of lower alkyl, specifically including methyl and a lower alkyl group of about 3-10 carbon atoms that is used as a linker to a fluorophore, such as a near infrared imaging agent, e.g., Cy 5. The carbonyl carbon at "a" may be also utilized for coupling of R1 or, especially, R3. R1 therefore includes a linker and a fluorophore.

R3, in Formula LI/P-2 above, is illustrated as a special case of R1, further including a non-natural amino acid selected from Table 2, which forms a P3 residue; the P3 residue may also be linked to a label.

P2 is either proline or a non-natural amino acid as shown in Table 2,

R2 is a capping group which has as the effect of preventing further chemical reactions from occurring at the capped site, and is a non-amino acid moiety bonded to the C- or N-terminal of the peptide chain. Examples of common N-terminal capping groups used in peptide synthesis are Boc (t-butoxycarbonyl,) and Cbz (benzyloxycarbonyl). Other capping groups useful in synthesis are acetyl and adamantyl, dimethyl benzyl succinimidyl, 4-methylbenzyl, 2-thiophenylmethyl, 4-thiazolylmethyl, 3,5-difluorobenzyl, etc. Exemplified in LP-1 and LP-2 is an ethyl group.

Thus, the present invention comprises a compound for inhibiting legmain, having a formula according to Formula I or Formula II below

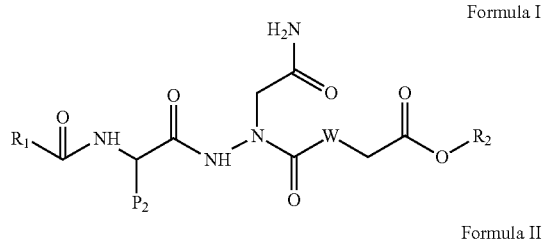

Formula I

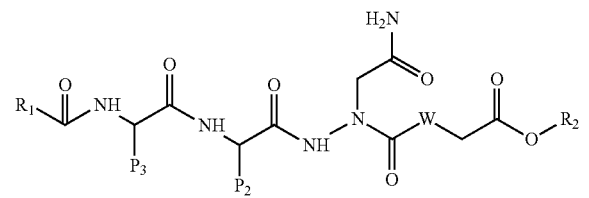

Formula II wherein, (a) R1 has the formula -linker-label, or -linker, where linker is lower alkyl, lower alkyl-aryl, or aryl, and label is a radiolabel or an optical label, said linker further optionally comprising a cell penetrating peptide;

(b) P3 is an amino acid side chain that is either leucine or a non-natural amino acid selected from the group consisting of (2furyl)alanine, (2thienyl)alanine, 4pyridylAla, 1amino1cyclohexane carboxylic acid, 1amino1cyclopentanecarboxylic acid, 2-Abz, 3Abz, 2Abu, 3amino3phenylpropionic acid, dehydroAbu, ACPC, Aib, AllylGly, Amb, Amc, Bip, Bpa, Cba, Cha, deltaLeu, deltaVal, Hyp, Igl, Inp, 1-Nal, 2-Nal, Nva, 4-nitroPhe, 4MethylPhe, 4Methyl-DPhe, Phe(pI), Phe4NH(Boc), hPhe, Phg, pip, Dpip, propargylglycine, Thz, Tic, Tle, 3-NitroTyr, Fmoc-L-neopentylglycine, Fmoc-pCl-L-Phe-OH, Fmoc-pBr-L-Phe-OH, Fmoc-4-amino-tetrahydropyran-4-carboxylic acid, Fmoc-L-Hol, Fmoc-Pip(Boc)-OH, Fmoc-L-styrylalanine, Fmoc-L-homoCha, Fmoc-L-Dab(Boc)-OH, Fmoc-L-Dapa(Boc)-OH, Fmoc-4-[2-(Boc-amino)ethoxy]-L-phenylalanine, and Fmoc-4-(tert-butoxycarbonylmethoxy)-L-phenylalanine;

(c) P2 is proline, or, in Formula I, proline or leucine or a non-natural amino acid as defined for P3;

(d) W has the formula of a double bond to its adjacent CH group or an epoxide group wherein W is C and an epoxide oxygen is bonded to it and an adjacent carbon; and (e) R2 selected from the group consisting of lower alkyl, aryl, and lower alkyl-aryl.

The compound may have the following formula:

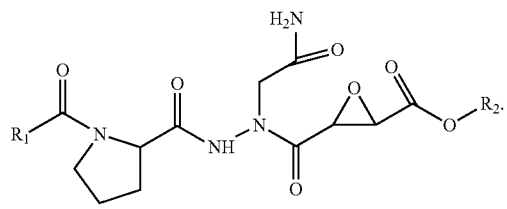

In any of the above, R1 may be lower alkyl linked to a fluorescent dye. The fluorescent dye may be Cy5. R1 may be linked to a dye and R2 may be ethyl. IN certain compounds according to the invention, W is a double bond and P2 is proline. R2 is one of ethyl, methyl, propyl or butyl.

The present invention also comprises a method of specifically inhibiting legumain activity, comprising the step of contacting the legumain with a compound according to the formulas set forth above. In this method, R1 may comprise a lower alkyl or aryl group without a label.

Certain aspects of the invention comprise using a compound according to the following:

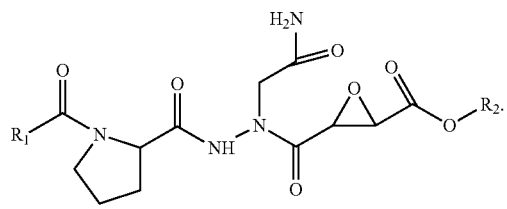

or a compound having the formula

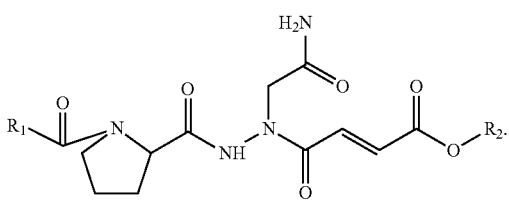

R1 and R3 may comprise lower alkyl linkers having between three and twelve atoms and a linkage to a label. Also, in certain aspects of the invention, R2 is one of ethyl, methyl, propyl or butyl.

Also provided is a method of imaging a tissue in an organism having active legumain in the tissue, comprising administering to the organism a compound according to the formulas above. In certain aspects of these methods, R1 is a linker to a fluorescent dye. In certain aspects of these methods said tissue being imaged comprises a tumor preferentially labeled by said compound.

Certain aspects of the invention comprise a composition suitable for administration in vivo, for imaging legumain activity in tissue, comprising a compound having an epoxide or n-Michael warhead, a peptidyl backbone with asparagine in p1 and proline in P2 and a label linked to said peptidyl backbone. This compound may be according to Formula I or Formula II as defined above.

In certain aspects of the invention, R1 may be defined as—lower alkyl-fluorophore (or label). Certain aspects of the invention comprise a method of specifically inhibiting legumain activity, comprising the step of contacting the legumain with a compound as described above. Certain aspects of the invention comprise a method of imaging a tissue in an organism having active legumain in the tissue, comprising administering to the organism a compound as described above. The organism may be a human or non-human animal. A label will be used to enable imaging, according to imaging methods described below. Certain aspects of the invention comprise a method of imaging a tissue in an organism having active legumain in the tissue, comprising administering to the organism a compound as described above having an R3 group, where R3 includes a label. A near-infrared label may be used.

DETAILED DESCRIPTION OF THE PREFERRED EMBODIMENT

Overview

Figure 1:
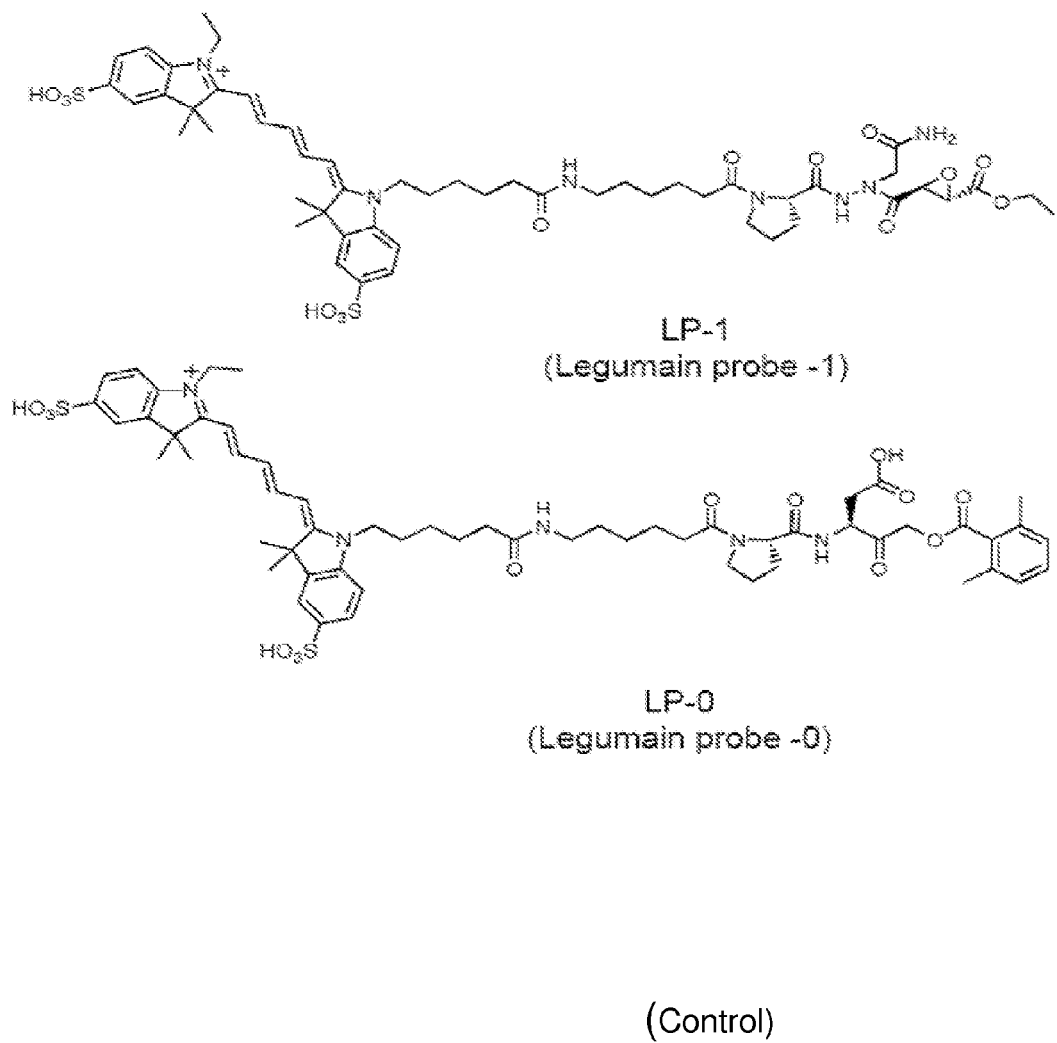
FIG. 1 shows structures of legumain inhibitors and probes.
Figure 1:
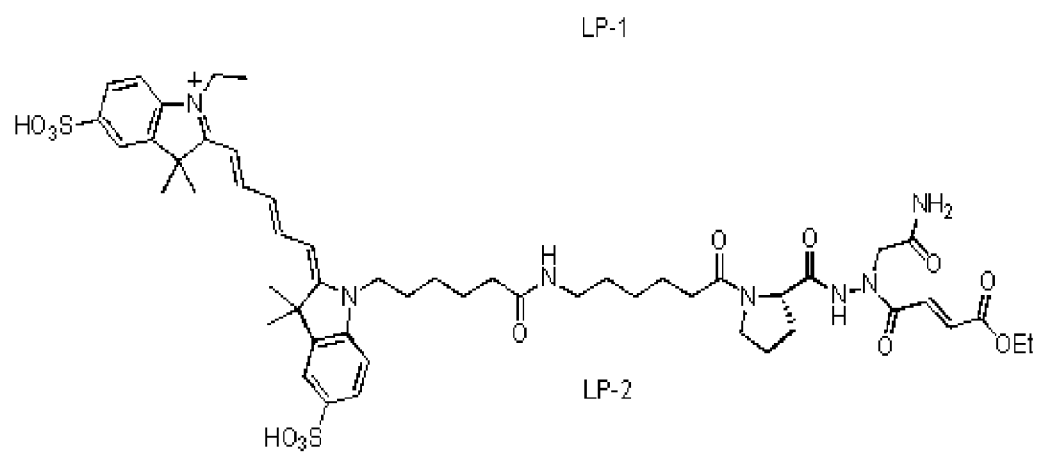
Figure 1:
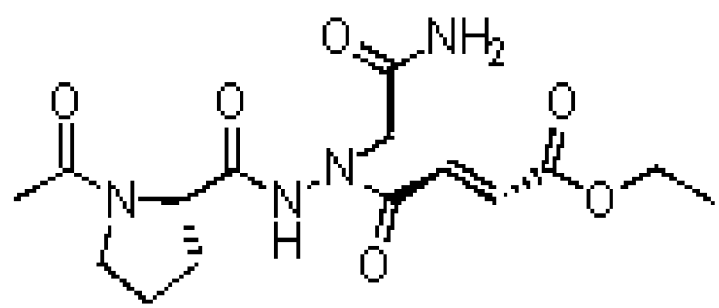

The present disclosure describes the design and in vivo application of fluorescently labeled activity based probes (ABPs) for legumain. It is shown that optimized aza-peptidyl Asn epoxides are highly selective and potent inhibitors that can be readily converted into Near infrared fluorescence— (NIRF) labeled ABPs for whole body, noninvasive imaging applications. It is further shown that these probes specifically label legumain in various normal tissues as well as in solid tumors when applied in vivo. Interestingly, addition of cell penetrating peptides to the probes enhanced cellular uptake but resulted in increased cross-reactivity towards other lysosomal proteases as the result of their accumulation in lysosomes. Overall, it is demonstrated that the present aza-peptidyl Asn ABPs are valuable new tools for the future study of legumain function in more complex models of human disease.

The examples below illustrate both an unlabeled and a near infrared fluorescence (NIRF)-labeled legumain probe, LP-I, which is a highly potent and selective inhibitor. The exemplified probe contains a Pro-Asn-aza epoxide scaffold that is distinct from the previously reported legumain inhibitors. When LP-I was used for non-invasive imaging applications, we were able to monitor legumain activity both in normal tissues and in solid tumors. Its favorable reactivity and clearance resulted in high contrast in tumors rapidly after probe injection. We were also able to track whole body distribution of the probe as well as the level of active legumain in organs by ex vivo imaging and SDS-PAGE. In addition, we tested a series of cell-permeabilizing moieties as a delivery strategy for ABPs. Although some of these moieties improved cell permeability and legumain labeling in cells, they also increased off-target labeling via enhanced lysosomal uptake and extended circulation times in vivo. LP1 and related probes provide a valuable new imaging probe with desirable in vitro and in vivo characteristics. This new imaging agent and its corresponding inhibitor are likely to prove valuable for future in vivo studies of legumain function.

DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "label" means a molecule attached to a legumain inhibitor such that it can be detected, e.g., by radioscintigraphy, X-ray, NMR, or other methods known in the art. The label may be a radiographic label or an optical label, i.e. detectible by its effect on light. Examples of labels include, for example, $^{18}F$, paramagnetic isotopes, x-ray labels, etc. Other optical labels which can be used include small molecules, such as biotin. In one preferred, embodiment, the inhibitor is labeled with an optical label that emits radiation at visual, IR, or near IR wavelengths. Examples of various optical (fluorescent) labels include, but are not limited to, fluorescein, lissamine, phycoerythrin, rhodamine, Cy2, Cy3, Cy3.5, Cy5, Cy5.5, Cy7, Fluor X, or others known in the art, such as those described in Haugland, Handbook of Fluorescent Probes and Research Chemicals, Molecular Probes, Inc.: Eugene, Oreg. (1996), incorporated herein by reference) Those of ordinary skill in the art will know of other suitable labels for binding to the present inhibitors, or will be able to ascertain such, using routine experimentation. Furthermore, the attachment of these labels to the inhibitors can be done using standard techniques common to those of ordinary skill in the art. The label may be attached by attached through using a linking group. The linking group may be attached covalently to the inhibitor and covalently or ionically to the label. For example, a label may be attached to the inhibitor by reacting with amino groups and other basic functional groups of the linker or inhibitor (e.g., lysine residues, terminal —$NH_2$ groups, etc.) and also be chelated to labels such as metal atoms.

Specifically included in the definition of label is Cy5, having the structure

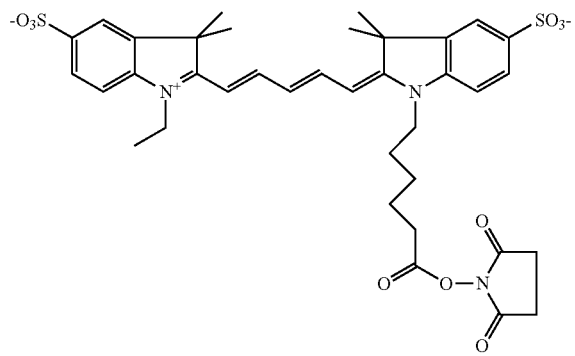

The term "legumain" means asparaginyl endopeptidase (EC 3.4.22.34), which shows strict specificity for hydrolysis of asparaginyl bonds. The term includes human legumain, gene symbol LGMN. Other legumain enzymes, i.e., from mouse, chimpanzee, Candidatus Methanoregula boonei, sorghum or other plants, or flatworms or other parasites are also included within this definition.

The term "alkyl", alone or in combination with other groups, refers to a branched or straight-chain monovalent (or divalent as a linker) saturated aliphatic hydrocarbon radical of one to twenty carbon atoms, preferably one to sixteen carbon atoms, more preferably one to ten carbon atoms. The term "lower alkyl", alone or in combination with other groups, refers to a branched or straight-chain alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred. The term lower alkyl includes substituted alkyl, such as "perfluoro-lower alkyl", which refers to a lower alkyl group wherein all of the hydrogens of the lower alkyl group are substituted or replaced by fluoro. Among the preferred perfluoro-lower alkyl groups are trifluoromethyl, pentafluoroethyl and heptafluoropropyl, with trifluoromethyl being especially preferred. Also included are "alkoxy", which the group R'—O—, wherein R' is alkyl. The term "lower-alkoxy" refers to the group R"—O—, wherein R" is lower-alkyl. Examples of lower alkoxy groups are e.g., methoxy, ethoxy, propoxy, isopropoxy, butoxy, isobutoxy and hexyloxy, with methoxy being especially preferred. Also included is "lower alkylthio", which refers to the group R'—S—, wherein R' is lower-alkyl as defined above and alkyl groups bridged by an amide linkage.

Specifically included in the definition of lower alkyl is a chain of 8-12 atoms which are carbon except for an amide linkage, as shown in FIG. 1.

The term "aryl" refers to an aromatic monovalent mono- or polycarbocyclic radical, such as phenyl and naphthyl, preferably phenyl. Substituted aryl is aryl which is mono-, di- or tri-substituted, independently, by lower alkyl, lower alkoxy, halogen, amino or perfluoro-lower alkyl, preferably by lower alkyl, lower alkoxy and halogen.

The present compounds may be made through the use of solid phase peptide synthesis techniques, which will employ known protective groups, capping groups, and the like. The term "capping group" refers to an alkyl or aryl group has the effect of preventing further chemical reactions from occurring at that site, and is a non-amino acid moiety bonded to the C- or N-terminal of the peptide chain. Examples of common N-terminal capping groups used in peptide synthesis are Boc (t-butoxycarbonyl,) and Cbz (benzyloxycarbonyl). Other capping groups useful in synthesis are acetyl and adamantyl, dimethyl benzyl succinimidyl, 4-methylbenzyl, 2-thiophenylmethyl, 4-thiazolylmethyl, 3,5-difluorobenzyl, etc. An example of preferred capping groups is the group consisting of Boc (t-butoxycarbonyl,), Cbz (benzyloxycarbonyl), adamantyl, dimethyl benzyl succinimidyl, 4-methylbenzyl, 2-thiophenylmethyl, 4-thiazolylmethyl, 3,5-difluorobenzyl, and lower alkyl.

The term "Michael acceptor" refers to any α,β-unsaturated compound which is capable of reacting with a nucleophile in a conjugate addition reaction such as the so called Michael addition. Strictly speaking, the term Michael addition refers to a particular conjugate addition reaction in which a carbanion is reacted with an α,β-unsaturated compound, whereas the present invention is primarily concerned with the situation when the nucleophile is a group at an active site in a protease. For example, acrylic acid esters, e.g., —C═CH—C(═O)—O-lower alkyl are especially suitable for use as Michael acceptor warheads in the present compounds. Also suitable and exemplified here are Michael acceptors of the formula —C(═O)—C═C—C(═O)—O-lower alkyl. The term "N-Michael acceptor" refers to a compound having a Michael acceptor warhead and an N-linked residue adjacent the warhead, as described e.g., in "Specificity of aza-peptide electrophile activity-based probes of caspases," K B Sexton, D Kato, A B Berger, M Fonovic, S H L Verhelst and M Bogyo, Cell Death and Differentiation (2007) 14, 727-732. An example of Michael acceptor warhead as used herein is

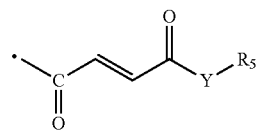

where Y is N or O and R5 is a capping group as defined in R2 above. The end carbonyl carbon is linked to a nitrogen bearing an amino acid side chain structure, e.g. Asparganine.

Overview
Probe/Inhibitor Structures

The present compounds are termed generally "probes" when attached to a label and "inhibitors" when no label is attached. Since the compounds bind to the active site of the enzyme, they will inhibit or inactivate an enzyme molecule bound to the compound. The portion of the compound which binds to the enzyme active site is termed the "warhead." The present warheads are either an epoxide or a Michael acceptor. The present compounds are distinguished from AOMK warheads; AOMK-based probes were found to generally be non-specific or unstable. A comparative example of an AOMK probe, termed "LP-0" is described. LP-0 has a dimethyl benzyl capping group; LP-1 and LP-2 have acetyl capping groups. Caps are R2 groups in the formulas above.

Additional portions of the compound include a substrate mimicking portion having amino acid residues, or moieties in the nature of amino acids. By convention, these residues are identified by their position relative to the enzyme's active site, which corresponds to the warhead in the present inhibitors. The position adjacent to the warhead is the P1; next removed is the P2 position, etc. The presently preferred compounds have Asn in P1 position and proline in the P2 position. The present compounds also use an aza structure (N—N) in which the P1 side chain is bound to nitrogen, rather than an alpha amino acid, as in a native peptide.

The presently preferred label is a fluorophore which can be used in vivo, i.e., with low hydrophobicity and high photostability, such as Cy5. Near infrared fluorescence (NIRF) has been found to be desirable for in vivo imaging, where light passes through tissue, around 0.65-1.4 μM in wavelength. It is contemplated that the present NIRF probes be used in animal research models and in human tissue. See, e.g., de Vries et al., "Multispectral Near-Infrared Fluorescence Molecular Imaging of Matrix Metalloproteinases in a Human Carotid Plaque Using a Matrix-Degrading Metalloproteinase—Sensitive Activatable Fluorescent Probe," (Circulation. 2009; 119: e534-e536) and Jaffer et al., "Molecular Imaging of Cardiovascular Disease," (Circulation. 2007; 116:1052-1061.)

Probe Activity

Disclosed below are activity based probes, i.e., they only label active enzyme. The probes are specific for legumain, and may be used to inhibit or inhibit and label active enzyme in situ. The compounds exhibit little or no activity towards caspases or cathepsins. It may be said, for example, the activity towards legumain will be on the order of at least 3 times greater for legumain than caspase 3, cathepsin B or cathepsin L, preferably at least 10 times greater, and even 100 times greater. Experimental data is given in Table 1 below. However, it must be noted that it was not possible to compare activity in numbers between different enzymes by measuring kobs/[I], and we were unable to do so except for legumain, because the inhibitors showed such a poor activity against other enzymes. It can be said that LI-1/LI-2 showed no inhibitory effect against other enzymes even at millimolar concentrations. LP-1 labeled cathepsins only at high concentrations or when legumain activity is suppressed and LP-2 did not label any cathepsins at high concentrations.

An additional property of the present compounds is that they have rapid binding kinetics.

Second order rate constants are given in Table 1 and show that the present compounds, depending on structure, will have approximately a 10- to 100-fold faster reaction time than the corresponding AOMK control. Faster reaction kinetics results in rapid probe binding and covalent modification, hence minimizing extended circulation and side effect especially in vivo. Previous probe was only tested in intact cells and not in vivo.

The present compounds may be further linked to a cell penetrating peptide, such as tat, for improved entry into cells.

The present compounds can be synthesized by solid phase synthesis techniques. These techniques are described below. Technical details of variations in these techniques may be found in literature relating to peptide synthesis. Further details on the synthetic methods described here may be found e.g., in Ref. 20. Described there is a solid phase approach for the synthesis of azapeptide inhibitors and activity based probes (ABPs) for cysteine proteases.

Cell Penetrating Peptide (tat)

The present methods and compounds may include cell penetrating peptides, which are exemplified by tat peptides, e.g., —Ac-RKKRRORRC (SEQ ID NO: 3) and penetratin. Cholesterol is also used for cell penetration. In tat, the Orn is a Glutamine in the native Tat sequence but ornithine is used here. Preferably the amino acids—except the cysteine used for linkage—are D-amino acids. Tat is an 86-amino acid protein involved in the replication of human immunodeficiency virus type 1 (HIV-1). The HIV-1 Tat transactivation protein is efficiently taken up by cells (Mann and Frankel, *EMBO*, 10: 1733-1739, 1991). A region of the Tat protein centered on a cluster of basic amino acids is responsible for this translocation activity (Vives et al., *J Biol. Chem.*, 272: 16010-16017, 1997). Tat peptide-mediated cellular uptake and nuclear translocation have been demonstrated in several systems. A synthetic peptide consisting of the Tat basic amino acids 48-60 with a cysteine residue at the C-terminus coupled to fluorescein maleimide has been shown to translocate to the cell nucleus as determined by fluorescence microscopy (Vives et al., *J. Biol. Chem.*, 272:16010-16017, 1997). A number of other cell permeability peptides are known, as disclosed, for example, in US 20060263382 by Hotchkiss et al., published Nov. 23, 2006, entitled "Membrane-permeant peptide complexes for treatment of sepsis." These sequences include RQARRNRRRRWRERQR-51 (SEQ ID NO: 4, HIV-1 Rev protein basic motif); MPKTRRRPRR-SQRKRPPTP-119 (SEQ ID NO; 5, HTLV-1 Rex protein basic motif; (Kubota et al., *Biochem. Biophys. Res. Comm.*, 162:963-970, 1989); the third helix of the homeodomain of Antennapedia (Derossi, et al., *J. Biol. Chem.* 271:18188-93, 1996) (43-RQILIWFQNRRMKWLL-58; a peptide derivable from the heavy chain variable region of an anti-DNA monoclonal antibody (Avrameas, et al., *Proc. Natl. Acad. Sci.* 95:5601-06, 1998) (VAYISRGGVSTYYSDTVKGR-FTRQKYNKRA (SEQ ID NO: 6; and the Herpes simplex virus VP22 protein (Elliot and O'Hare, *Cell,* 88:223-33, 1997). Other examples of sequences with favorable cell uptake include arginine-rich permeation peptide sequences based on the Tat basic peptide, such as: acetyl-RKKRRN-RRR-AHA-epsilon.KGC-amide (SEQ ID NO: 7); acetyl-RKKRROrnRRR-AHA-.epsilon.KGC-amide (SEQ ID NO: 8); acetyl-RKKRRERRR-AHA-.epsilon.KGC-amide (SEQ ID NO: 9) and acetyl-RKKRRNorleuRRR-AHA-.epsilon.KGC-amide AcrrrrrrrrC (SEQ ID NO: 10); where Orn is ornithine and Norleu is norleucine. Octaarginine (R8) and penetratin are exemplified below. Further details on penetratin (6 NH2-RQIKIWFQNRRMKWKK-CONH2) (SEQ ID NO: 11) are given in Nucleic Acids Research, 2003, Vol. 31, No. 2 556-561. Other permeant peptides disclosed there as useful include poly-Arg, RRRRRRRRR (SEQ ID NO: 12); amphipathic polycationic peptide, RAARRAARR (SEQ ID NO: 13); and the viral permeation peptide, PLSSIFSRIGDP (SEQ ID NO: 14).

The cell penetrating peptide may also comprise a short (3-10 residues) stretch of charged amino acids, such as Lys, Arg, Asp and Glu. Another preferred embodiment includes a peptide having 6-10 arginine residues. The exact sequence can be varied insofar as no specific recognition sequence is known to be required.

Label

A variety of labels may be attached to the present inhibitors, so that binding of the inhibitor to a legumain may be visualized and also localized within a tissue or individual cell. The label is a molecule or molecular complex which is bonded to the present probe and provides a signal which can be detected and localized to the location of the active legumain where the probe has bound. The signal is proportionate to the amount of active legumain in a given location. Exemplified below is a fluorescent dye for in vivo or intracellular labeling. This permits their use in methods where selected legumain enzymes are activated in disease states associated with such activation, e.g., tumors or atherosclerotic lesions.

Labels for use with the present compounds may include near infrared dyes such as a cyanine dye (e.g., Cy5), which is described in the working examples of the preferred embodiment, or another useful imaging agent such as magnetic imaging agents or radioactive imaging agents. Cy5 is Cy5-bis-OSU, N,N'-biscarboxypentyl-5,5'-disulfonatoindodicarbocyanine, Amersham Life Science, catalog No. PA15000. Cy5 can exist in a variety of related structures, such as shown in Tu et al., "The influence of fluorescent dye structure on the electrophoretic mobility of end-labeled DNA," *Nucleic Acids Research* 26(11):2797-2802 (1998), and also incorporated here by reference.

The label used should be suitable for in vivo imaging. Cy5 was used here for near infrared imaging. Also suitable are a family of cyanine dyes, Cy2, Cy3, Cy5, Cy7, and their derivatives, based on the partially saturated indole nitrogen heterocyclic nucleus with two aromatic units being connected via a polyalkene bridge of varying carbon number. These probes exhibit fluorescence excitation and emission profiles that are similar to many of the traditional dyes, such as fluorescein and tetramethylrhodamine, but with enhanced water solubility, photostability, and higher quantum yields. Most of the cyanine dyes are more environmentally stable than their traditional counterparts, rendering their fluorescence emission intensity less sensitive to pH and organic mounting media. In a manner similar to the Alexa Fluors, the excitation wavelengths of the Cy series of synthetic dyes are tuned specifically for use with common laser and arc-discharge sources, and the fluorescence emission can be detected with traditional filter combinations.

The cyanine dyes are readily available as reactive dyes or fluorophores coupled to a wide variety of secondary antibodies, dextrin, streptavidin, and egg-white avidin. The cyanine dyes generally have broader absorption spectral regions than members of the Alexa Fluor family, making them somewhat more versatile in the choice of laser excitation sources for confocal microscopy.

Alternatively, the present methods may comprise the in vivo administration of a positron emitter, where the present compounds are useful in PET imaging of legumain-active tissues, which is here intended to include related techniques such as SPECT. The radiolabel is advantageously selected from the group consisting of: $^{131}$I, $^{99m}$TC, $^{111}$In, $^{18}$F, $^{64}$Cu, $^{76}$Br, $^{86}$Y, $^{55}$Co and $^{124}$I and $^{125}$I.

These metals may be bound by chelation to the peptide binding agents of the present invention. In particular, these include radionuclides having decay properties that are amenable for use as a diagnostic tracer or for deposition of medically useful radiation within cells or tissues. Conjugated coordination complexes of the present caspase binding agents may be prepared with a radioactive metal (radionuclide). The radioactive nuclide can, for example, be selected from the group consisting of radioactive isotopes of Tc, Ru, In, Ga, Co, Pt, Fe, Os, Ir, W, Re, Cr, Mo, Mn, Ni, Rh, Pd, Nb, Cu and Ta. Exemplary isotopes include Tc-99m, Tc-99, In-111, Ga-67, Ga-68, Cu-64, Ru-97, Cr-51, Co-57, Re-188, I-123, I-125, I-130, I-131, I-133, Sc-47, As-72, Se-72, Y-90, Y-88, Pd-100, Rh-100 m, Sb-119, Ba-128, Hg-197, At-211, Bi-212, Pd-212, Pd-109, Cu-67, Br-75, Br-76, Br-77, C-11, N-13, O-15, F-18, Pb-203, Pb-212, Bi-212, Cu-64, Ru-97, Rh-105, Au-198, and Ag-199 and Re-186.

Further discussion of radioactive labels is found in U.S. Pat. No. 6,589,503 to Piwnica-Worms, issued Jul. 8, 2003, entitled "Membrane-permeant peptide complexes for medical imaging, diagnostics, and pharmaceutical therapy." Radionuclides that are useful for medical imaging of activated caspases include $^{11}$C ($t_{1/2}$ 20.3 min), $^{13}$N ($t_{1/2}$ 9.97 min), $^{18}$F ($t_{1/2}$ 109.7 min), $^{64}$Cu ($t_{1/2}$ 12 h), $^{68}$Ga ($t_{1/2}$ 68 min) for positron emission tomography (PET) and $^{67}$Ga ($t_{1/2}$ 68 min), $^{99m}$Tc ($t_{1/2}$ 6 h), $^{123}$I ($t_{1/2}$ 13 h) and $^{201}$Tl ($t_{1/2}$ 73.5 h) for single photon emission computed tomography (SPECT) (Hom and Katzenellenbogen, *Nucl. Med. Biol.*, 1997, 24:485-498. These metals are coupled to the present peptide like structures. Such coupling is done by preparing conjugated coordination complexes. The peptide metal coordination complexes can be readily prepared by methods known in the art, e.g., as described in the above-referenced patent. For example, a caspase inhibitor peptide to be conjugated to a linker and a metal chelating moiety can be admixed with a salt of the radioactive metal in the presence of a suitable reducing agent, if required, in aqueous media at temperatures from room temperature to reflux temperature, and the end-product coordination complex can be obtained and isolated in high yield at both macro (carrier added, e.g., Tc-99) concentrations and at tracer (no carrier added, e.g., Tc-99m) concentrations (typically less than $10^{-6}$ molar). As is known, when (Tc-99m) pertechnetate (TcO$_4$) is reduced by a reducing agent, such as stannous chloride, in the presence of chelating ligands such as, but not restricted to, those containing N$_2$ S$_2$, N$_2$ SO, N$_3$ S and NS$_3$ moieties, complexes of (TcO)N$_2$ S$_2$, (TcO)N$_2$ SO, (TcO)N$_3$ S and (TcO)NS$_3$ are formed (Meegalla et al., *J Med. Chem.*, 1997, 40:9-17.

Chelation sites on the present peptide-like structures may be provided as described, e.g., in U.S. Pat. No. 6,323,313 to Tait, et al., issued Nov. 27, 2001, entitled "Annexin derivative with endogenous chelation sites." This method involves adding certain amino acid residues such as cysteine and glycine to the active sequence. Another method is disclosed in U.S. Pat. No. 5,830,431 to Srinivasan, et al., issued Nov. 3, 1998, entitled "Radiolabeled peptide compositions for site-specific targeting." This patent discloses a radiolabeled peptide characterized by having its carboxy terminal amino acid in its carboxylic acid form whereby the peptide is coupled to a diagnostic or therapeutic radionuclide by a chelating agent. The chelating agent is capable of covalently binding a selected radionuclide thereto. Suitable chelating agents generally include those which contain a tetradentate ligand with at least one sulfur group available for binding the metal radionuclide such as the known N$_3$ S and N$_2$ S$_2$ ligands. More particularly, chelating groups that may be used in conjunction with this method and other involving the present compounds include 2,3-bis(mercaptoacetamido)propanoate (U.S. Pat. No. 4,444,690), S-benzoylmercaptoacetylglycylglycylglycine (U.S. Pat. No. 4,861,869), dicyclic dianhydrides such as DTPA and EDTA and derivatives thereof (U.S. Pat. No. 4,479,930), NS chelates containing amino groups to enhance chelation kinetics (U.S. Pat. No. 5,310,536), N$_2$ S$_2$ chelates as described in U.S. Pat. No. 4,965,392, the N$_3$ S chelates as described in U.S. Pat. No. 5,120,526, and the N$_2$ S$_2$ chelates containing cleavable linkers as described in U.S. Pat. No. 5,175,257. The chelating agent is coupled to the peptide-like portion of the present compounds by standard methodology known in the field of the invention and may be added at any location on the peptide provided that the specific active caspase binding activity of the peptide is not adversely affected. Preferably, the chelating group is covalently coupled to the amino terminal amino acid of the peptide. The chelating group may advantageously be attached to the peptide during solid phase peptide synthesis or added by solution phase chemistry after the peptide has been obtained. Preferred chelating groups include DTPA, carboxymethyl DTPA, tetradentate ligands containing a combination of N and S donor atoms or N donor atoms. This method is useful for a variety of radionuclides, including copper.

Also, as described in Thakur et al., "The Role of Radiolabeled Peptide-Nucleic Acid Chimeras and Peptides in Imaging Oncogene Expression," *Indian Journal of Nuclear Medicine*, 2004, 19(3):98-114, $^{64}$Cu may be chelated by methods described for $^{99}$Tc, by adding $^{64}$CuCl$_2$ in 0.1M HCL to purified inhibitor in 0.1M ammonium citrate, pH 5.5, incubation for 20 min at 90° C., quenching with EDTA and purification by size exclusion chromatography.

Labeling with $^{18}$F may be carried out as described in Schottelius et al., "First $^{18}$F-Labeled Tracer Suitable for Routine Clinical Imaging of sst Receptor-Expressing Tumors Using Positron Emission Tomography," *Clinical Cancer Research*, Jun. 1, 2004, Vol. 10, 3593-3606. The chemoselective formation of an oxime bond between a radiohalogenated ketone or aldehyde, e.g., 4-[$^{18}$F]fluorobenzaldehyde, and a peptide functionalized with an aminooxy-functionality is disclosed. This methodology has been applied for radioiodination of antibodies (Kurth M, Pelegrin A, Rose K, et al "Site-specific conjugation of a radioiodinated phenethylamine derivative to a monoclonal antibody results in increased radioactivity localization in tumor," *J Med Chem*, 1993, 36: 1255-61) and has been proposed for the radioiodination of small peptides (Thumshirn G, Hersel U, Goodman S L, Kessler H. "Multimeric cyclic RGD peptides as potential tools for tumor targeting: solid-phase peptide synthesis and chemoselective oxime ligation," *Chemistry Eur J*, 2003, 9: 2717-2725).

As can be seen from the foregoing, the terminal groups R1 and R2 in Formulas LI/P-1, LI/P-2 or LI/P-3 may be modified to accommodate a chelation site. R1 may be a peptide chelation site containing about 4 amino acids selected from Cys and Gly. R2 may be —COOH, etc.

Kits

The present imaging agents may be provided in kits for measuring specific legumain activity. They may also be used to identify other inhibitory drugs by competition with the present probes and labels. A kit may be provided which contains a series of AFC-based peptide substrates according to the present description as fluorogenic indicators for assaying caspase protease activities. The label AFC (7-amino-4-trifluoro methylcoumarin) is known for use with protease substrates. Cleavage of the fluorophore results in increased fluorescence, with a shift of excitation and emission maxima to longer wavelengths. AMC and AFC appear to give identical sensitivity. The kit contains a 96, 384 or other size well plate in which a series of AFC-based caspase substrates are coated with both positive and negative controls. It provides the best solution for profiling caspases or caspase inhibitors. The kit may also contain a cell lysis buffer; assay buffer; AFC (fluorescence reference standard for calibration); and a detailed protocol.

Another kit format utilizes the fact that both caspase-3 and caspase-7 have substrate selectivity for the amino acid sequence Asp-Glu-Val-Asp (DEVD). This kit uses caspase 3-7 selective substrates as the fluorogenic indicator for assaying caspase-3/7 activities. Upon caspase-3/7 cleavage, the substrate generates the coumarin (e.g., AFC fluorophore) which has bright blue fluorescence and can be detected at excitation/emission=380 nm/500 nm. A bi-function assay buffer in this kit is designed to lyze the cells and measure the enzyme activity at the same time. Thus, this kit can measure caspase-3/7 activity in cell culture directly in a 96-well or 384-well plate. The kit may also contain a caspase 8 or 9 substrate.

Another kit format provides active legumain which cleave the substrates to release free AFC, which can then be quantified using a microtiter plate reader. Potential inhibitory compounds to be screened can directly be added to the reaction and the level of inhibition of caspases can then be determined. The assays can be performed directly in microtiter plates.

Another kit provides a formulation suitable for in vivo administration. The compounds of formulas I and II may be administered intravenously as a sterile liquid. The compound may be formulated with excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

Modified and Substituted Amino Acids

The Asn, proline and non-natural amino acids used in the present compounds may also be chemically modified. For example, amino groups may be acylated, alkylated or arylated. Benzyl groups may be halogenated, nitrosylated, alkylated, sulfonated or acylated. The natural side chains may be further modified. For example, one may use chemically modified amino acids may be incorporated into the present compounds, such as acetylated amino acids, e.g. N-acetyl-L-arginine; N-acetyl-L-proline; and hydroxylated amino acids such as 4-hydroxy-L-proline

EXAMPLES

Example 1

Design of Legumain Probes for In Vivo Applications

A scaffold was created that could be used to make probes that were highly selective for legumain with virtually no cross reactivity for other lysosomal proteases or related CD clan proteases such as caspases. In the past, our group developed activity based probes that can be used to label legumain in cell culture models (14). These first generation probes make use of the acyloxymethyl ketone (AOMK) group to covalently modify the active site cysteine and a Pro-Asp peptide for specific recognition by legumain. This peptide sequence was chosen based on the finding that, although legumain prefers processing of substrates at asparagine residues, it also binds to probes with a P1 aspartic acid (16). Since P1 Asn AOMKs are highly unstable (17), we originally focused our attention on the P1 Asp AOMK probes. These reagents, while useful for labeling legumain, have overall slow binding properties and generally low potency. In addition, P1 Asp-AOMKs are highly effective labels of caspases both in vitro and in vivo (18, 19). Described here are new peptide sequences, that have more selective binding properties such as are required for imaging probes to be of use. The prior art is focused on inhibitors and the selectivity is not demonstrated in vivo (7). The unique aza scaffold also allows incorporation of a P1 Asn (asparagine) residue without causing overall instability of the compound.

The present example describes the synthesis of an activity based probe LP-1 (Legumain Probe-1) that contains the aza-Asn epoxide and the P2 Pro of the first generation AOMK probe as well as a Cy5 fluorophore for in vivo imaging applications (FIG. 1). We also synthesized a Cy5-labeled version of the previously reported probe Biotin-PD-AOMK (LP-O, FIG. 1) for direct comparison with LP-1. LP-1 was synthesized via a previously reported solid-phase synthesis technique (20) and the Cy5 fluorophore was conjugated to the purified peptide at the final step (Scheme 1, FIG. 13). To directly compare enzyme specificity and kinetics between LP-1 and the previously described AOMKs, we also synthesized acetyl-capped inhibitor versions of LP-1 and LP-O (LI-1 and LI-O respectively; FIG. 1).

Example 2

Synthetic Methods

Unless otherwise noted, all resins and reagents used in the present examples were obtained from commercial suppliers and used without further purification. All solvents used were HPLC-grade and also purchased from commercial suppliers. Reactions were analyzed by LC/MS performed on an Agilent 1100 liquid chromatography system with an AP1150EX single quadrupole mass spectrometer (Applied Biosystems). HPLC purifications were carried out using an AKTA explorer 100 (Amersham Pharmacia Biotech) with CIS reversed-phase columns (Waters). Mobile phase consisted of 95:5: 0.1=water:acetonitrile:trifluoroacetic acid (solvent A) and 0.1% trifluoroacetic acid in acetonitrile (solvent B). High-resolution mass spectrometry (HRMS) was performed using an LTQFTMS (Thermo Fisher Scientific). Matrix-assisted laser desorption ionization time of flight (MALDI-TOF) mass spectrometry was performed using a Broker Autoflex TOF/TOF mass spectrometer (Broker). IC$_{50}$ measurements and enzyme kinetics assays were performed on a Spectramax M5 fluorescent plate reader (Molecular Devices). Fluorescent gels were scanned with a Typhoon 9400 flatbed laser scanner (GE Healthcare). Male BALB/c nude mice (4-8 weeks old) were obtained from Charles River and housed in the research animal facility at the Stanford University Department of Comparative Medicine. All animal protocols were approved by the Stanford Administrative Panel on Laboratory Animal Care, and the procedures were performed in accordance to their guidelines. In vivo imaging experiments were performed using the IVIS 200 imaging system (Xenogen) and ex vivo imaging experiments were performed using the FMT 2500 system (VisEn Medical).

Peptidyl Aza-Asn epoxide was synthesized by following the previously reported procedure (20) on a Rink SS resin (Advanced ChemTech). Peptidyl Asp AOMK was synthesized by the previously reported procedure (15). Each carrier-probe conjugate was synthesized by following the previously reported procedure (18). The tat peptide and the penetratin peptide were custom synthesized by the Stanford PAN peptide synthesis facility. All synthesized peptides were cleaved from resin by applying cleavage cocktail containing 95% TFA and purified by HPLC. The purified peptides were then coupled with Cy5-NHS (1 eq) in DMSO with DIEA (5 eq) for 1 hr and purified by HPLC. The purity and identity of all compounds were assessed by LC-MS and HR-Characterization data of final compounds was obtained to confirm their identity (data not shown).

General Methods for Solid Phase Peptide Synthesis.

AOMK inhibitor (LI-0) and probe (LP-0) were synthesized as described previously in Kato, D., Boatright, K. M., Berger, A. B., Nazif, T., Blum, G., Ryan, C., Chehade, K. A., Salvesen, G. S., and Bogyo, M. (2005) Activity-based probes that target diverse cysteine protease families, *Nat Chem Biol* 1, 33-38.

All aza-peptidyl epoxide inhibitor (LI-1) and probes (LP-1, tat LP-1, r8 LP-1, penetratin LP-1 and cholesterol LP-1) were synthesized by following the previously reported procedures (Kato, D., Verhelst, S. H., Sexton, K. B., and Bogyo, M. (2005) A general solid phase method for the preparation of diverse azapeptide probes directed against cysteine proteases, *Org Lett* 7, 5649-5652; Edgington, L. E., Berger, A. B., Blum, G., Albrow, V. E., Paulick, M. G., Lineberry, N., and Bogyo, M. (2009) Noninvasive optical imaging of apoptosis by caspase-targeted activity-based probes, *Nat Med* 15, 967-973) with slight modifications. Fmoc protecting groups from Rink SS resin (0.75 mmol/g) were removed by treatment with 20% piperidine in DMF for 15 min, followed by three washes with DMF. A 1.2 M solution of bromoacetic acid (10 eq) in NMP and DIC (10 eq) were added to the resin. The resin was shaken 1.5 hrs and washed three times. A solution of Mono-Fmoc protected hydrazide (3 eq) in NMP was added and shaken overnight. Resin loading was determined by Fmoc-quantification (0.2-0.3 mmol/g). A 0.5M solution of N-Fmoc-protected amino acid (3 eq.) and HOBt (3 eq.) in DMF and DIC (3 eq.) were added to the resin. The resin was shaken 1.5-2 hrs. For each of the following steps, Fmoc-deprotection and coupling reactions were repeated as described above. Capping of N-terminal amine was achieved by shaking the resin with a 0.5 M solution of acetic anhydride (5 eq.) and DIEA (5 eq.) in DMF for 5 min General Method of Cleavage from the Resin and Purification of Peptides.

The 3-way nylon stopcock was replaced with polypropylene Needle Valve (Waters). A solution of 95% TFA/2.5% TIS/2.5% $H_2O$ was added to the resin. After standing for 1 h, the cleavage mixture was collected, and the resin was washed with the fresh cleavage solution and 1:1 mixture of water and acetonitrile. The combined fractions were evaporated and the crude residue was purified by HPLC. Fractions containing product were collected and lyophilized to dryness.

Synthesis of LP-1 ctrl

Figure 14:
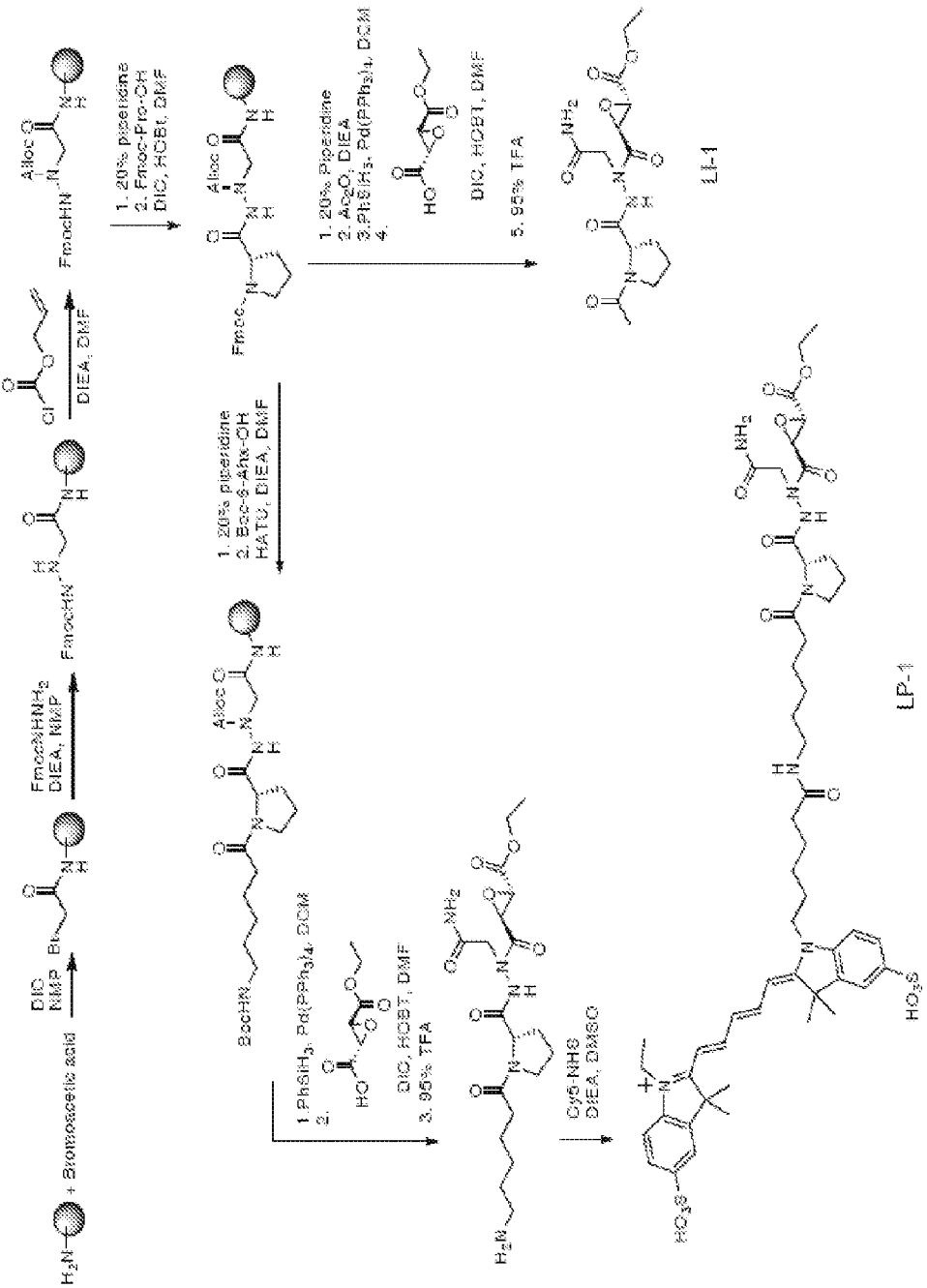
FIG. 14 is a schematic diagram showing the synthesis of LI-1 and LP-1 on a solid support. The compound is linked to the support through the Asn residue. As can be seen, the identity of residue P2 (proline in this case) is determined by the selection of the residue added, and can be varied as desired. Similarly, the linker can be selected as desired, as well as the label attached to the linker.
Figure 15:
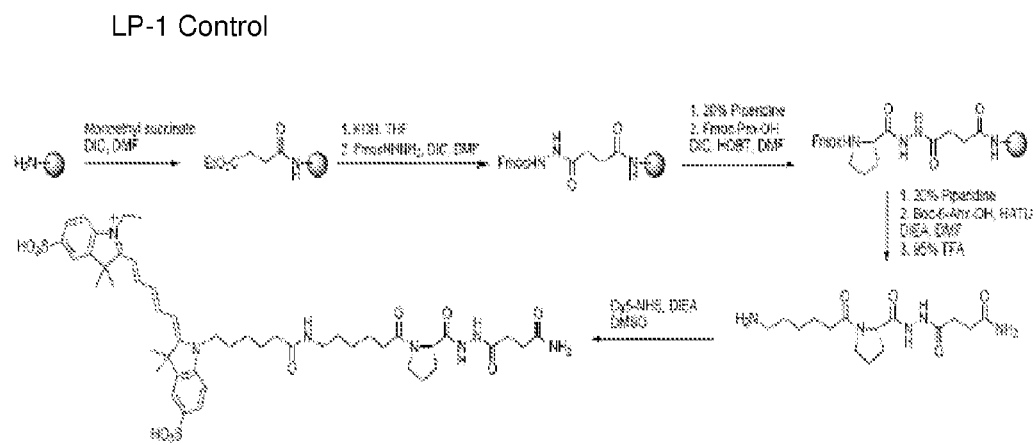
FIG. 15 is a reaction scheme showing the synthesis of the LP-1 control, which lacks a warhead portion and the Asn side chain.

LP-1 ctrl was synthesized by following Scheme 1 (FIG. 14). Rink SS resin was deprotected and loaded with monoethyl succinate (5 eq) and DIC (5 eq) in DMF for 2 hrs. The rest of the amino acids were added successively and the final product was purified by following the same methods described above.

Characterization of all Compounds.

All final compounds used for biological studies were purified by HPLC and characterized by either [a]high-resolution mass spectrometry (HRMS) or [b]MALDI-TOF.

LI-1 $[M+H]^+$ calcd. for $C_{15}H_{23}N_4O_7$, 371.1567. found 371.1568[a]

LI-0 $[M+H]^+$ calcd. for $C_{21}H_{27}N_2O_7$, 419.1818. found 419.1816[a]

LP-1 $[M+H]^+$ calcd. for $C_{52}H_{70}N_7O_{14}S_2$, 1080.4422. found 1080.4692[a]

LP-0 $[M+H]^+$ calcd. for $C_{58}H_{74}N_5O_{14}S_2$, 1128.4674. found 1128.4711[a]

LP-1 Ctrl $[M+H]^+$ calcd. for $C_{48}H_{66}N_7O_{11}S_2$, 980.4262. found 980.4435[a]

tat LP-1 $[M+H]^+$ calcd. for $C_{123}H_{203}N_{42}O_{29}S_3$, 2828.4863. found 2828.61[b]

r8 LP-1 $[M+H]^+$ calcd. for $C_{118}H_{193}N_{44}O_{28}S_3$, 2770.4188. found 2770.42[b]

Penetratin LP-1 $[M]^+$ calcd. for $C_{174}H_{261}N_{45}O_{40}S_4$, 3748.8655. found 3748.9038[a]

Cholesterol LP-1 $[M+H]^+$ calcd. for $C_{92}H_{133}N_{10}O_{18}S_3$, 1761.8956. found 1762.12[b]

Cathepsin Immunoprecipitation

Figure 16:
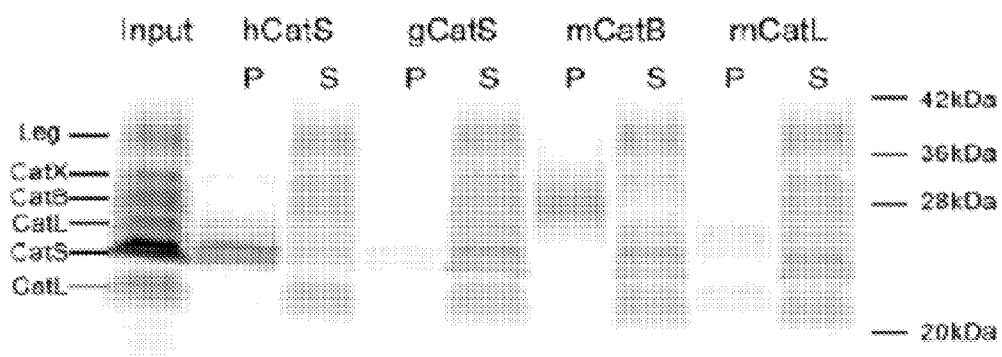
FIG. 16 is a photograph of a gel showing immunoprecipitation of cathepsins in intact raw 264.7 cells by antibodies to those cathepsins.

Immunoprecipitation of cathepsins in intact raw 264.7 cells. Cells were pre-treated with 100 µM of LI-1 for 1 hr and labeled by addition of LP-1 (25 µM). High concentration of LP-1 was used to bring out all the off-target labeling in intact cells. The results of an immunoprecipitation experiment comparing activity of LP-1 against cathepsins S, B and L is shown in FIG. 16.

RAW 264.7 macrophages (600,000 cells/well) were seeded in a 6 well plate 24 hrs prior to labeling. Cells were pre-treated with 100 µM of LI-1 for 1 hr and labeled by addition of LP-1 (25 µM). High concentration of LP-1 was used to bring out all the off-target labeling in intact cells. Cells were washed with PBS buffer and lysed by addition of citrate-phosphate lysis buffer (50 mM citrate-phosphate, 1% CHAPS, 0.5% Triton, 5 mM DTT, pH 4.5). 20 µL of crude lysates were diluted to 500 ml in RIPA buffer (phosphate-buffered saline, 0.5% NP-40, 1 mM EDTA, pH 7.4). Anti-mouse cathepsin B (E Weber Halle), anti-mouse cathepsin L (R&D Systems), anti-goat cathepsin S (Abchem) and anti-human cathepsin S (R&D Systems) were added and mixed for 15 mM at 0° C. 40 µL of Protein A/G Plus Agarose beads (Santa Cruz Biotechnology) were added and mixed overnight at 4° C. Samples were spun down and supernatant and beads were separated. Beads were washed with RIPA buffer and boiled after addition of sample buffer 2× (20% glycerol, 100 mM Tris HCl, pH 6.8, 6% SDS, and 10% b-mercaptoethanol). Acetone was added to the supernatant and kept at −80° C. for 2 h. Precipitated proteins were collected by centrifugation in the cold for 30 min, dried, and dissolved by boiling in sample buffer. Samples without immunoprecipitation (input), pellets (P) and supernatant (S) were separated on a 12.5% SDS-PAGE and visualized by scanning of the gel with a Typhoon flatbed laser scanner (excitation/emission 633/680 nm).

Example 3

Selectivity and Potency of Legumain Inhibitors and Probes

To determine the overall potency and selectivity of the aza-epoxide and AOMK inhibitors we performed inhibition studies for both compounds against recombinant legumain, cathepsin B, cathepsin L and caspase-3 (Table 1).

Inhibition of various cysteine proteases by LI-1 and LI-0.

| Inhibitor | Legumain IC$_{50}$ | Legumain k$_{obs}$/[I] | Cathepsin B IC$_{50}$ | Cathepsin L IC$_{50}$ | Caspase-3 IC$_{50}$ |
|---|---|---|---|---|---|
| LI-1 | 11.5 nM | 72352 M$^{-1}$s$^{-1}$ | 390 μM | 220 μM | 890 μM |
| LI-0 | 704 nM | 1586 M$^{-1}$s$^{-1}$ | >1 mM | >1 mM | 2.8 μM |
| JPM-OEt[a] | N/D | | 0.78 μM | 2.98 μM | N/D |
| Z-DEVD-FMK[b] | N/D | | N/D | N/D | 0.13 μM |

[a]JPM-OEt is a broad-spectrum cathepsin inhibitor.
[b]Z-DEVD-FMK is a caspase-3 specific inhibitor.

Simple IC50 determination showed that LI-1 (IC50=11.5 nM) is 70 fold more potent than LI-O (ICso=704 nM) against legumain, while both compounds showed very weak activity against cathepsin B (IC50=390 μM for LI-1 and greater than 1 mM for LI-O) and cathepsin L (IC50=202 μM for LI-1 and higher than 1 mM for LI-O). Importantly, LI-O showed a significant inhibitory effect (IC50=2.8 μM) on caspase-3 while LI-1 showed nearly no inhibition (IC50o=890 μM). To further evaluate the kinetics of inhibition of legumain by the two classes of inhibitors we also measured second-order rate constants ($k_{obs}$ [I]) for both compounds (Table 1). As expected, ($k_{obs}$ [I])=72350 M$^{-1}$s$^{-1}$) inhibited legumain approximately 50-fold faster than LI-O ($k_{obs}$ [I])=1585 M$^{-1}$s$^{-1}$). These results confirmed that incorporation of P1 Asn via aza-peptidyl scaffold greatly enhanced efficiency and specificity of inhibition by LI-1 compared to the P1 Asp AOMK scaffold. The rapid inhibition kinetics of the aza-Asn epoxide scaffold is advantageous for in vivo imaging as it allows rapid binding to legumain thus providing a better signal to noise ratio even for probes with relatively short half-lives in vivo. This allows the use of lower overall doses of probe and prevents extended circulation that can possibly cause cross reactivity with other proteases.

Determination of IC$_{50}$ against cysteine proteases and second order rate constants (kobs1[I]) for legumain Activity of legumain was measured with the fluorogenic substrate, Cbz-Ala-Ala-Asn-AMC (Anaspec), cathepsin B and cathepsin L was measured with Cbz-Phe-Arg-AMC (Bachem), and caspase-3 was measured with Caspase-3 Substrate VII (Calbiochem). Assay buffers consist of 20 mM citric acid, 60 mM disodium hydrogen orthophosphate, 1 mM EDTA, 0.1% CHAPS, 4 mM DTT, pH 5.8 for legumain, 50 mM dihydrogen sodium orthophosphate, 1 mM EDTA, 5 mM DTT, pH 6.25 for cathepsin B and cathepsin L and 100 mM Tris, 0.1% CHAPS, 10% sucrose, 10 mM DTT, pH 7.4 for caspase-3. Concentrations of substrates during the measurement were 1O~M (legumain, cathepsin L and caspase-3) and 50~M (cathepsin B) and concentration of enzymes were 100 nM for cathepsin L and caspase-3, 270 nM for legumain and 360 nM for cathepsin B. Each enzyme was incubated with inhibitor concentrations ranging from 1 nM to 1 mM in the presence of the substrates. The increase in fluorescence was continuously monitored every 30 see for 2.5 hrs with a Spectramax M5 fluorescent plate reader (Molecular Devices), and inhibition curves were recorded. IC$_{50}$ values were calculated by plotting the normalized enzyme activity against the inhibitor concentration at 60 min for legumain and at 30 min for caspase-3, cathepsin B and cathepsin L using nonlinear regression analysis (GraphPad Prism). ICso values with known broad-spectrum cathepsin inhibitor (JPM-OEt) and caspase-3 inhibitor (Z-DEVD-FMK) were also measured for comparison. All measurements were performed in triplicate and the average values were reported.

Second-order inhibition rate constants were determined by following the previously described method in the literature (6). The pseudo-first-order rate constants ($k_{obs}$) were obtained from plots of ln vJ Vo versus time where Vo is the rate of hydrolysis of fluorogenic substrate and Vt is the rate of hydrolysis of substrate in the presence of the inhibitor. The second-order inhibition rate constants were calculated using the following equation. Second order rate constant=(kobs1 [I])(1+[S]/K$_m$)

Example 4

Labeling of Active Legumain in Intact Cells

Figure 2:
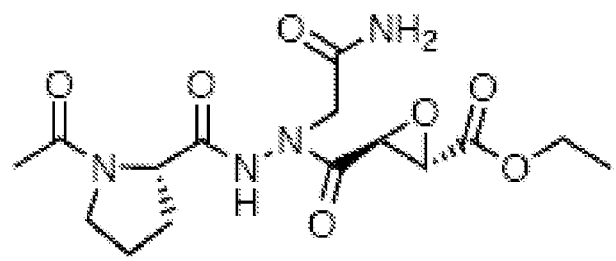
FIG. 2 shows structures of Aza-Asn epoxide legumain inhibitor, LI-1 and legumain probe, LP-1 compared to Asp-AOMK inhibitor, LI-O and probe, LP-O.
Figure 2:
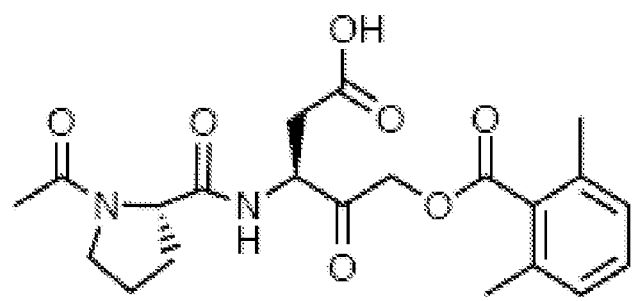
Figure 3:
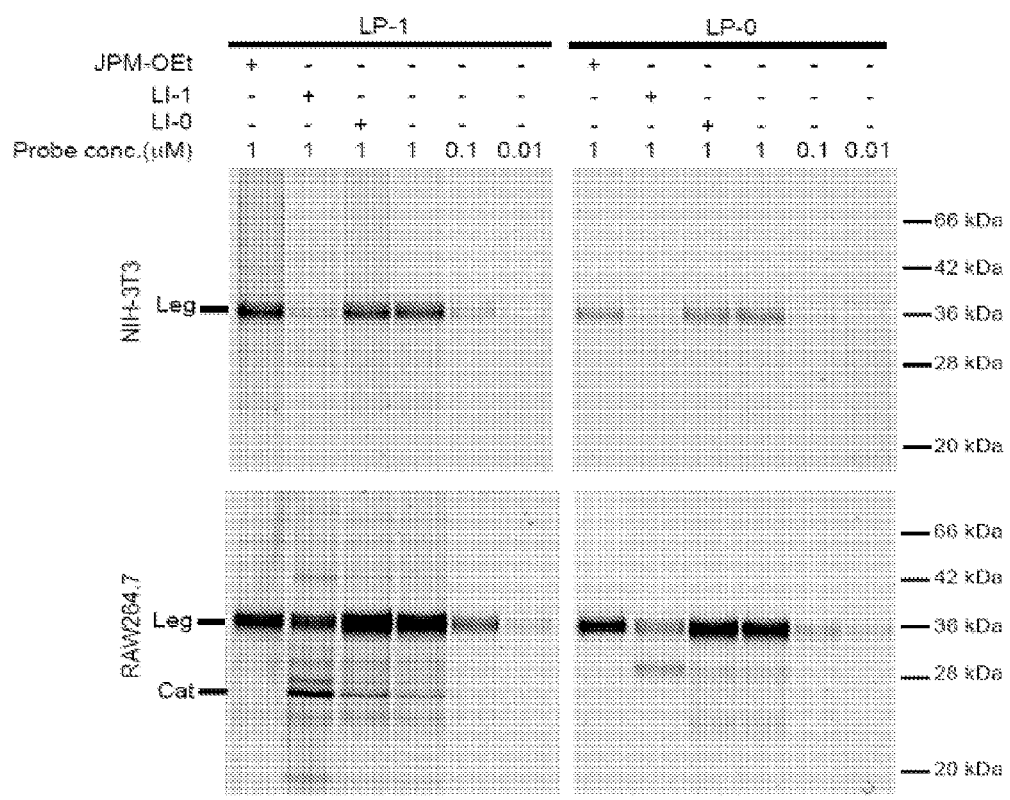
FIG. 3 shows gels of direct labeling of legumain in intact cells by LP-1 and LP-O. Intact monolayers of NIH-3T3 fibroblasts (top) or RAW 264.7 macrophages (bottom) were pre-treated with the cathepsin inhibitor JPM-OEt (10 µM; first column), the legumain inhibitors LI-O/LI-1 (10 µM; second and third columns) and labeled by addition of LP-1 and LP-O at the indicated concentrations.

We treated intact NIH-3T3 and RAW 264.7 cells with LP-1 and LP-O respectively and monitored protein labeling using SDS-PAGE followed by scanning of the gel to detect the Cy5 fluorescence (FIG. 2). Both probes selectively labeled active legumain in NIH-3T3 fibroblasts. As previously observed in the enzyme kinetic assays, LP-I labeled active legumain more efficiently than LP-0 at low probe concentrations and showed overall stronger labeling signals. Interestingly, when the two probes were used to label RAW 264.7 macrophages, both showed some degree of cross reactivity towards lysosomal cathepsins. The identity of these off targets as cathepsins was confirmed by pre-treatment of cells with the broad-spectrum cathepsin inhibitor JPM-OEt (21) and further verified by immunoprecipitation (FIG. 16). Although some degree of cross reactivity of AOMK probes towards cathepsins has been reported (15), attempts to inhibit cathepsins with various aza-epoxide inhibitors have been unsuccessful (22). Therefore, the labeling of cathepsins by LP-I was particularly surprising. That is, these data suggest that even though the present compounds may have very low potency toward a particular protease target in vitro, when added to cells that actively accumulate the probes in their lysosomes, such as macrophages, they are able to react with other abundant proteases. Furthermore, when cells were pre-treated with legumain inhibitors we observed more intense cathepsin labeling. This could be explained by the fact that cathepsins are known to be substrates for legumain (3, 23), thus legumain inhibition could result in increased levels of cathepsins and therefore increased non-specific labeling by the legumain probes. While the cathepsin cross reactivity is not ideal, by using lower probe concentrations and more potent inhibitor scaffolds, it should be possible to obtain selective labeling of legumain in vivo. Based on these results, we decided that LP-I would be the optimal reagent for in vivo imaging studies as it has faster kinetics and its overall higher potency, resulting in less background labeling of cathepsins and caspases.

RAW 264.7 cells (250,000 cells/well) and NIH-3T3 cells (200,000 cells/well) were seeded in a 24 well plate 24-30 hrs prior to labeling. Cells were pre-treated with appropriate inhibitors for 1.5 hrs and labeled by addition of each probe for 1 hrs; the final DMSO concentration was maintained less than 0.2%. Cells were washed with PBS buffer and lysed by addition of sample buffer. Crude lysates were collected and separated by 12.5% SDS-PAGE. Labeled proteins were analyzed by scanning the gel with a Typhoon flatbed laser scanner (ex. 633 nM/em. 680 nM). For lysates labeling, cytosolic lysates of RAW 264.7 cells were prepared as previously described (29). Lysates were diluted to 1 mg/ml in 50 mM citrate phosphate buffer (pH 4.5), 0.1% CHAPS, 5 mM DTT and subjected to direct labeling. 25~L of lysates samples were pretreated with inhibitors for 30 min and labeled with probes for another 30 min. The labeled samples were separated by 12.5% SDS-PAGE and analyzed by scanning the gel with a Typhoon flatbed scanner.

Example 5

In Vivo Imaging of Legumain Using the Aza-Epoxide Probe LP-1

Figure 4:
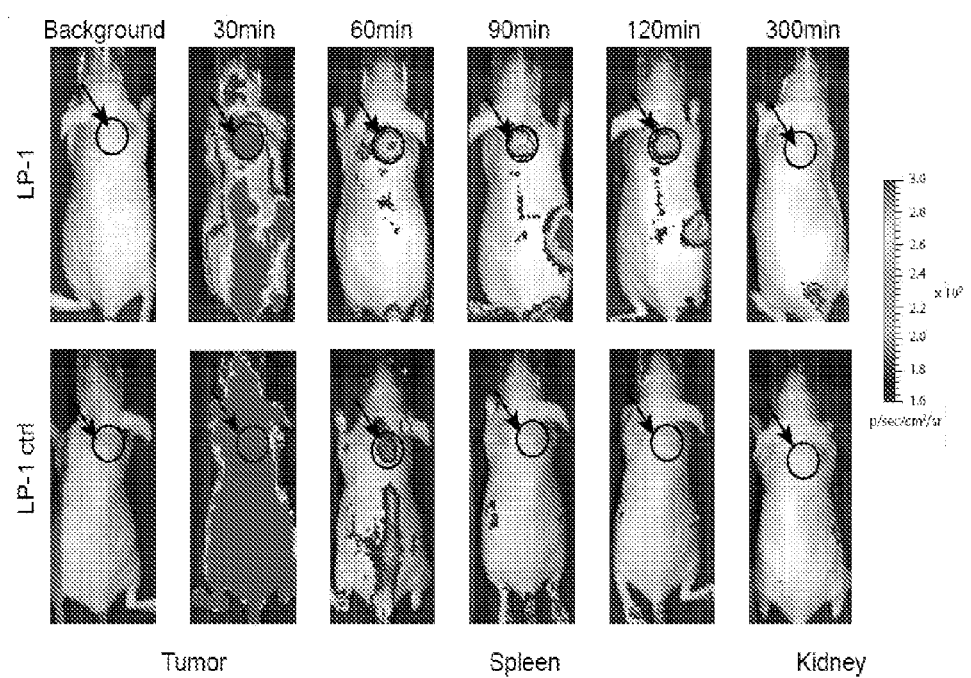
FIG. 4 shows photographs illustrating in vivo imaging of active legumain. Mice bearing C2C12/ras xenograft tumors were IV injected with LP-1 (top) or LP-1-ctrl (bottom) probes and mice imaged at the indicated time points. Shown to the left is a scale which, in the original, is presented using a colorimetric scale based on photons per second per centimeter square per steradian ($p\ S^{-1}\ cm^{-2}\ sr^{-1}$) overlaid on bright light images.
Figure 5:
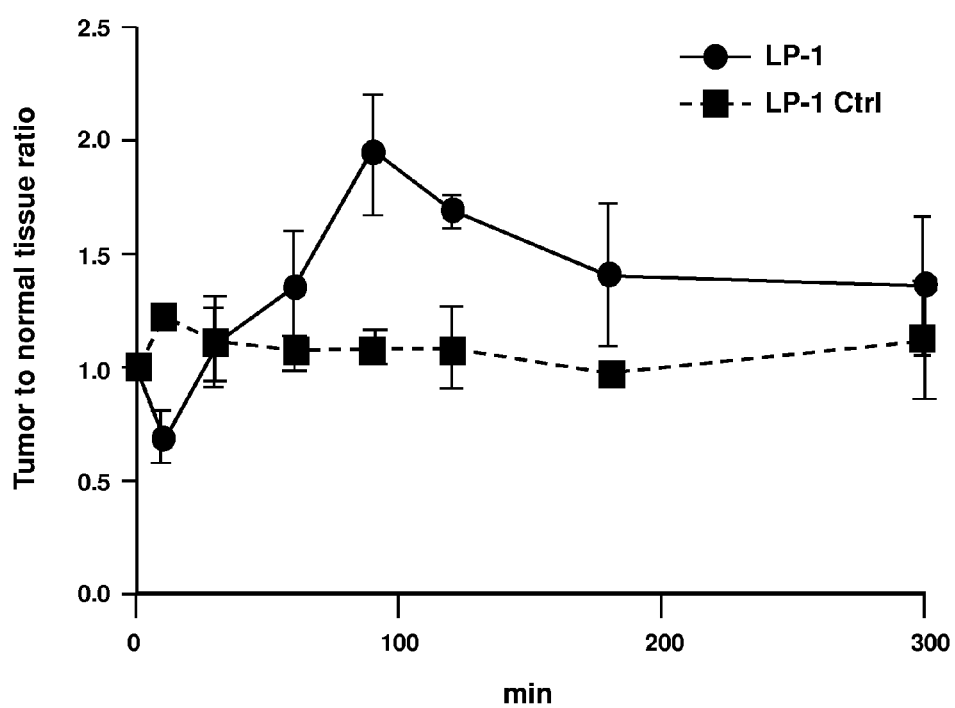
FIG. 5 is a graph that shows tumor to normal tissue signal ratio calculated from the mice labeled with LP-1 (circle symbols with a solid line) and LP-1 Ctrl (square symbols with a dotted line). Ratios were calculated from multiple mice (n=3 for LP-1 and n=2 for LP-1 Ctrl) and represent mean±standard error.

In order to examine in vivo properties of LP-1 and monitor active legumain levels non-invasively, we performed imaging experiments using a simple tumor xenograft model (C2C 1 2/Hras 1)(24). To verify that the in vivo fluorescent signal from LP-1 is legumain-specific we also used a control probe (LP-1 ctrl) that lacks the reactive epoxide group and therefore does not covalently bind to legumain. Mice were injected with the probes via tail vein and fluorescent images were collected over the course of 5 hrs. As expected, LP-1 rapidly accumulated in tumor tissues whereas LP-1 ctrl did not show such accumulation (FIG. 4). Quantification of the tumor to normal tissue ratio from the fluorescent images showed that LP-1 accumulated in tumors with a maximum signal to background ratio obtained at around 90 min (FIG. 5). Furthermore, the specific legumain signal was reduced to background levels after 120 min. This is in contrast to the previously reported cathepsin probes which only provide contrast after 8-12 hours and signals are retained beyond 48 hours. These data suggesting that legumain may have a more rapid rate of turn-over than the cathepsins and that the legumain probes have faster binding and clearance properties that leads to more rapid signal over background.

Figure 6:
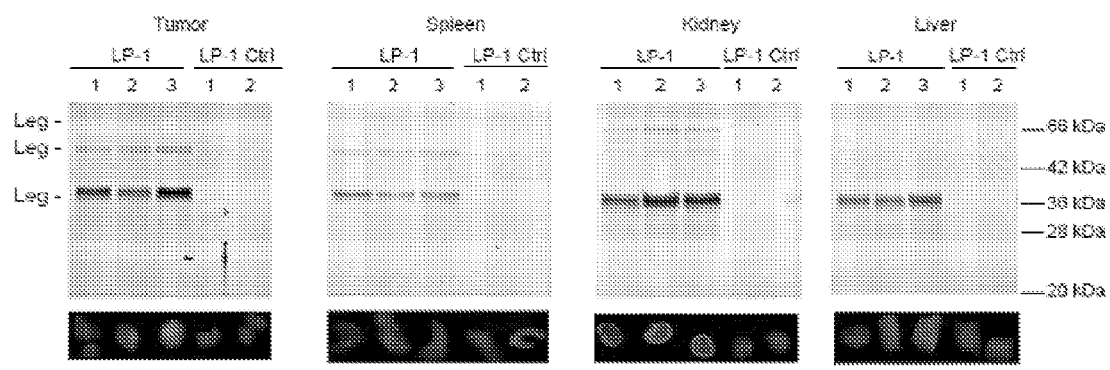
FIG. 6 is a series of photographs from gels that show ex vivo imaging of organs and protein labeling analyzed by SDS-PAGE. Fluorescently labeled proteins were visualized by scanning of the gel using a flatbed laser scanner. Each column represents an organ from individual mouse collected after in vivo imaging experiments.
Figure 7:
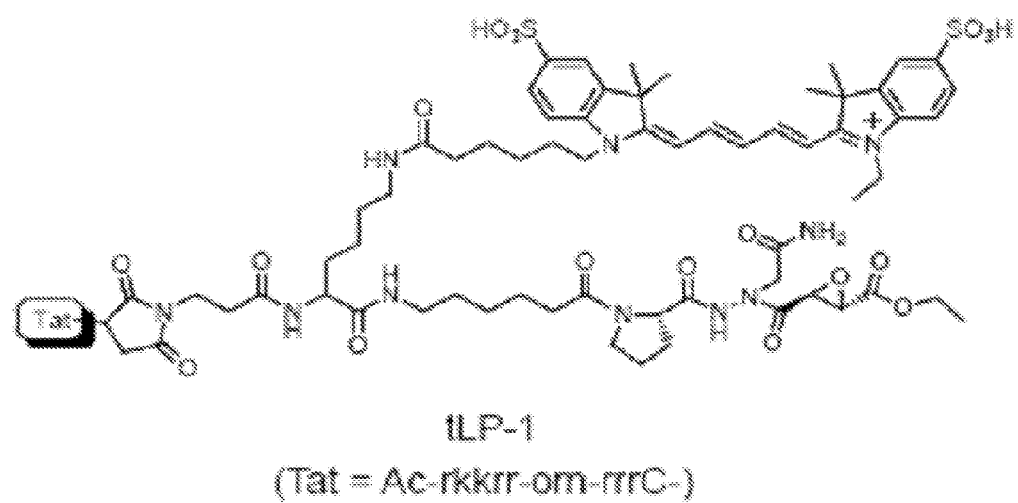
FIG. 7 shows the structure of tat-conjugated LP-1 (tLP-1). The tat sequence is given in single amino acid letter code, and orn is ornithine. Small letters are D-form residues.

At the end of the imaging time-course, we collected organs and carried out ex vivo imaging and SDS-PAGE analysis of extracts to confirm selective labeling of legumain by LP-1 (FIG. 6) Importantly, fluorescent images of each tissue showed that levels of active legumain directly correlated with the intensity of legumain labeling as measured by SDS-PAGE analysis. The result also demonstrated that LP-1 is remarkably selective toward legumain in vivo and showed virtually no off-target labeling. These data further support our hypothesis that using a more potent and kinetically fast binding scaffold, allows selective labeling of legumain in vivo.

In vivo/ex vivo imaging and SDS-PAGE analysis of organ lysates was conducted as follows: Tumor bearing mice were prepared by following the previously described method (24). C2C12/Hras1 or MDA-MB 231 MFP cells ($2 \times 10^{-6}$ cells/mouse) were injected subcutaneously on 4-8 week old male BALB/c nude mice. 14 days after transplantation, each probe (25 nmol in 100~L of sterile PBS) was injected via the tail vein into tumor-bearing mice. Mice were imaged at various time points after injection using the IVIS 200 imaging system equipped with a Cy5.5 filter. Relative fluorescence of equal-sized areas of tumor and background were measured using Living Image software (Caliper life science). Upon finishing the last time point of imaging, mice were anesthetized and sacrificed by cervical dislocation. Tumors, livers, kidneys and spleens were collected and imaged ex vivo by using the FMT 2500 with a Cy5 filter. After ex vivo imaging, organs were lysed by a dounce homogenizer in muscle lysis buffer (1% Triton X-100, 0.1% SDS, 0.5% sodium deoxycholate, 0.2% sodium azide in PBS, pH 7.2). Total protein extracts (100~g each) were separated by SDS-PAGE and visualized by scanning the gel with a Typhoon flatbed laser scanner.

Example 6

Use of a tat Peptide to Increase Cellular Uptake

Figure 8:
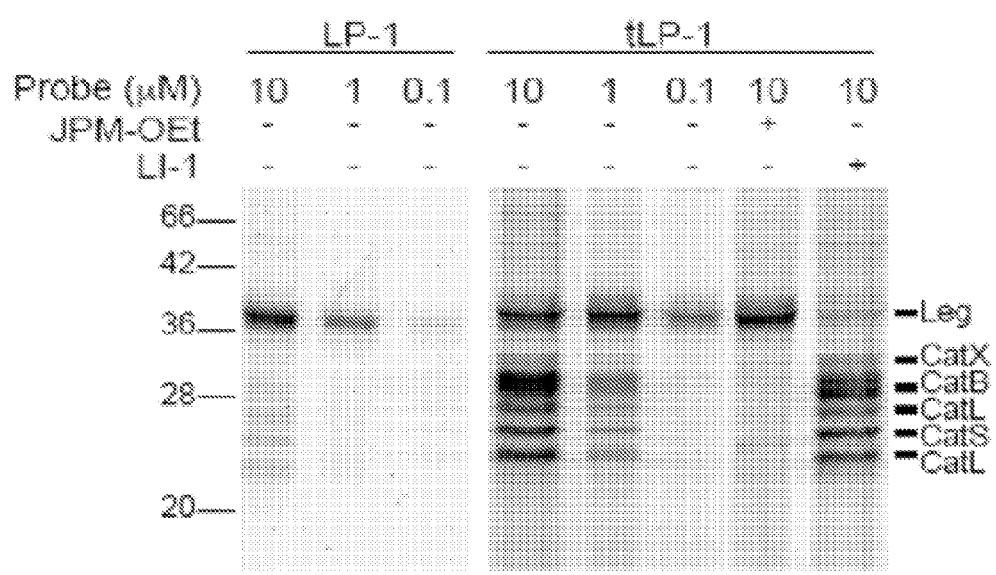
FIG. 8 is a pair of photographs from gels that show direct labeling of legumain in intact RAW 264.7 macrophages with LP-1 and tLP-1. Due to the differences in molecular weight between the two probes (approximately 1800), tLP-1 labeled legumain is slightly shifted on the gel relative to LP-1 labeled legumain. Where indicated, cells were pre-treated with either the general cathepsin inhibitor JPM-OEt or the legumain specific inhibitor LI-1.
Figure 9:
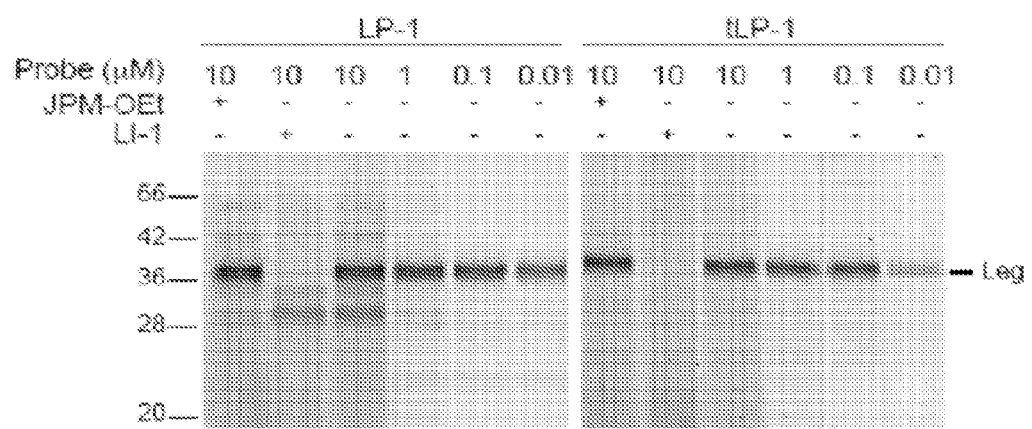
FIG. 9 is a pair of photographs from gels that shows a comparison of labeling legumain in RAW cell lysates by LP-1 and tLP-1.
Figure 10:
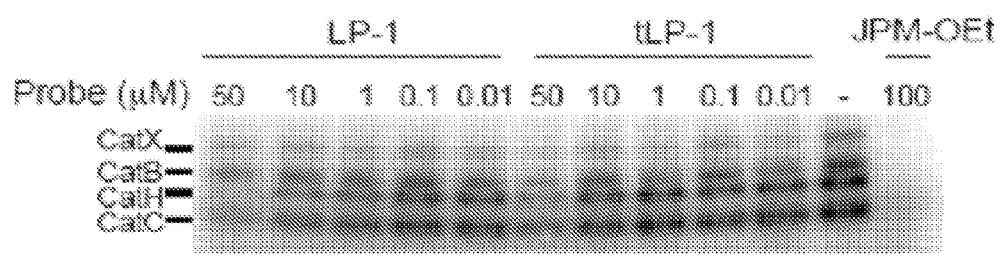
FIG. 10 is a photograph from a gel that shows competitive inhibition of cathepsins by LP-1 and tLP-1. RAW cell lysates were pre-treated with LP-1 and tLP-1 at the indicated concentrations and labeled by the general cathepsin probe $^{125}$I-DCG04.

Previously we reported that conjugating the tat peptide to an activity-based probe that targets caspases enhanced cell permeability, however, it also increased lysosomal uptake due to its positive charge. Thus the use of the tat carrier inadvertently increased cross-reactivity toward legumain (18). Inspired by this result, we conjugated the tat peptide to LP-1 to further improve its in vitro and in vivo reactivity toward legumain. To our surprise, when tested against intact RAW 264.7 macrophages, tat conjugated LP-1 (tLP-1; FIG. 8) labeled not only legumain but also multiple cathepsins, even at low concentrations (FIG. 8). We believe that this cross-reactivity results from increased lysosomal uptake and is not the result of a loss of specificity as the result of addition of the tat peptide. To test this hypothesis, we labeled RAW cell lysates with LP-1 and tLP-1 (FIG. 9). SDS-PAGE analysis confirmed that there is no difference in reactivity towards legumain for these two probes. We also performed a competition assay by pre-treating RAW lysates with each probe and labeling with the general cathepsin probe, $I^{125}$_DCG04 (25). These results further confirmed that both LP-1 and tLP-1 are equally poor inhibitors of the cathepsins (FIG. 10). Thus, the increased cross reactivity towards cathepsins is likely due to significant accumulation of the tLP-1 in the lysosome.

Figure 11A:
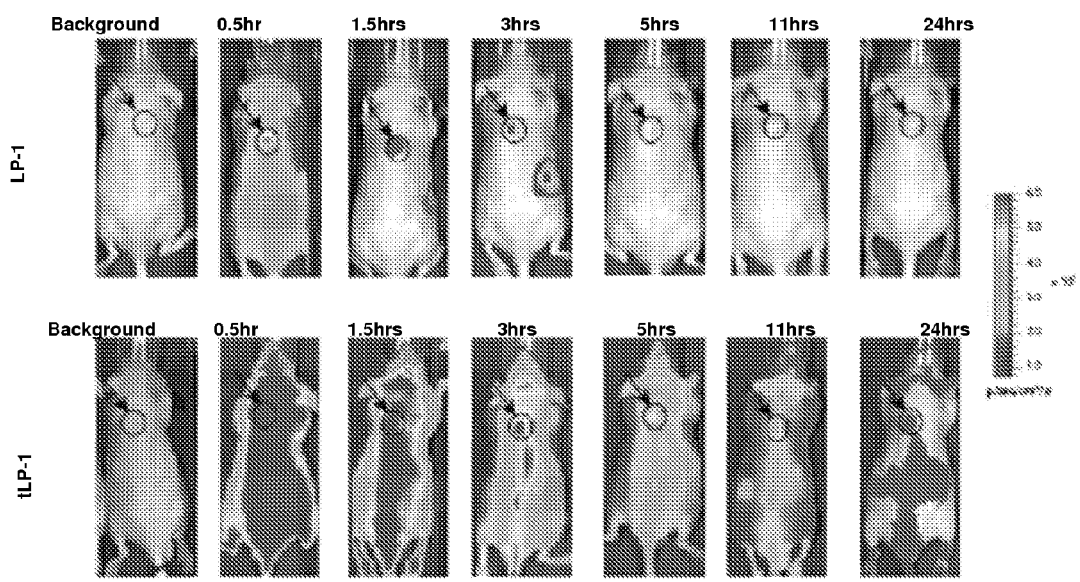
FIG. 11 shows in vivo imaging of legumain using LP-1 and tLP-1. Mice bearing C2C12/ras xenograft tumors were IV injected with LP-1 ((FIG. 11A, top) or tLP-1 (FIG. 11A, bottom) probes and mice imaged at the indicated time points. Images are presented using a colorimetric scale based on photons per second per centimeter square per steradian ($p\ S^{-1}\ cm^{-2}\ sr^{-1}$) overlaid on bright light images.
FIG. 11B shows corresponding gels illustrating biochemical characterization of in vivo labeled legumain. Fluorescently labeled proteins from tissue homogenates were visualized by scanning of the gel using a flatbed laser scanner. Each column represents an organ from an individual mouse collected after in vivo imaging experiments FIG. 12 is a photograph from a gel showing results with different carrier-conjugated LP-1 activity-based probes, r8 LP-1, where LP1-R=AcrrrrrrrrC (SEQ ID NO: 1), small letters indicating D-amino acids; penetratin-LP-1, where penetratin LP-1 R=Ac-RQIKIWFQNRRMKWKKC (SEQ ID NO: 2), and cholesterol LP-1, in a direct comparison between the carrier-conjugates. Intact RAW 264.7 macrophages (top) and NIH-3T3 fibroblasts (bottom) were labeled with each probe at the indicated concentrations. Total probe labeled proteins were visualized by SDS-PAGE followed by scanning of the gel using a flatbed laser scanner. The location of legumain (Leg) and cathepsins (Cat) are indicated. The unconjugated probes labeled legumain as well as the conjugated probes; conjugation with one of the carriers increased off-target binding to the cathepsins shown. The carrier should be selected to limit off-target binding, and may be tested according to the described method.
Figure 11B:
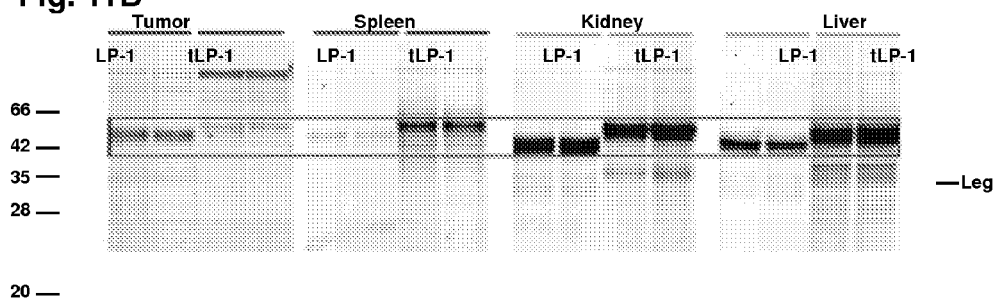

Since tLP-1 showed high cross-reactivity toward cathepsins in cells, we wanted to monitor its in vivo distribution and labeling kinetics compared to LP-1. We performed in vivo imaging and found that, although the tat peptide enhanced overall uptake of the probe, tLP-1 failed to show the selective uptake in tumors observed for LP-1. In addition, the tat peptide dramatically increased overall probe distribution and reduced the rate of clearance (FIG. 11A). As a result, tLP-I showed increased non-selective labeling in vivo relative to LP-I (FIG. 11B).

Example 7

Use of Additional Carrier-Conjugates on Legumain Probes

Cell-penetrating peptides (CPPs) and membrane targeting moieties have proven to be useful delivery methods for various biological reagents (26, 27). In addition to the tat peptide, we also decided to test several additional carrier molecules with our legumain probes. We chose octa-arginine (r8) and penetratin due to their widespread use as carriers. We also chose cholesterol since it has high affinity for membrane raft domains and has been used to enhance membrane permeability (28). The carrier conjugated LP-1 had the structures

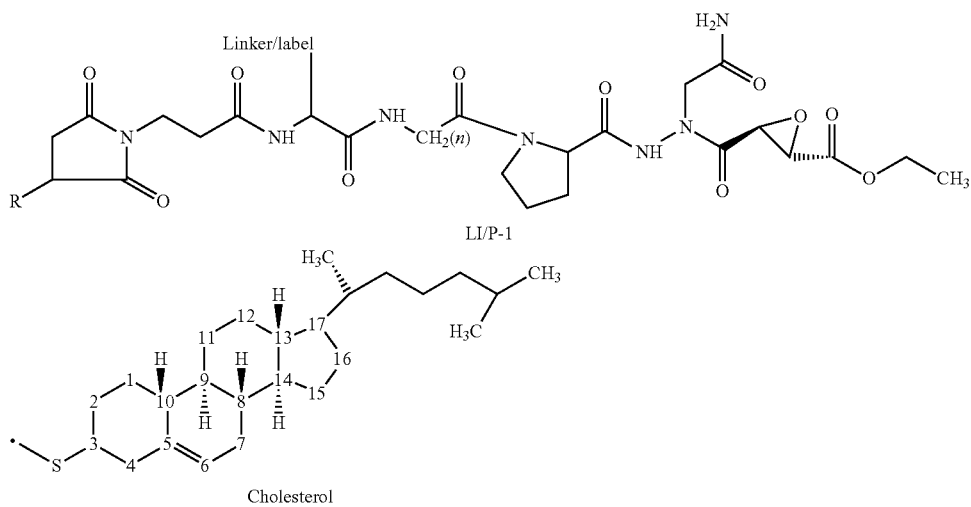

Cholesterol

In the above, R is either Ac-rrrrrrrr-C (SEQ ID NO: 1), in r8 LP-1; Ac-RQIKIWFQNRRMKWKKC- (SEQ ID NO: 2) in penetratin LP-1; or the cholesterol structure shown above in cholesterol LP-1. The Linker/label had the structure shown below, linked through the alkyl chain as in LP-1 shown in FIG. 1. In $CH_2$ (n), n is 5. The length of this chain could be varied in other embodiments, e.g. n=2-7.

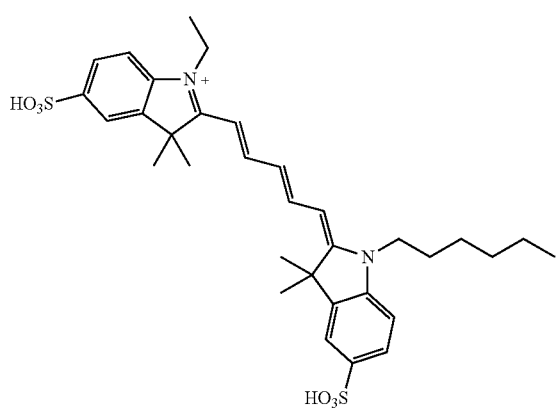

Figure 12:
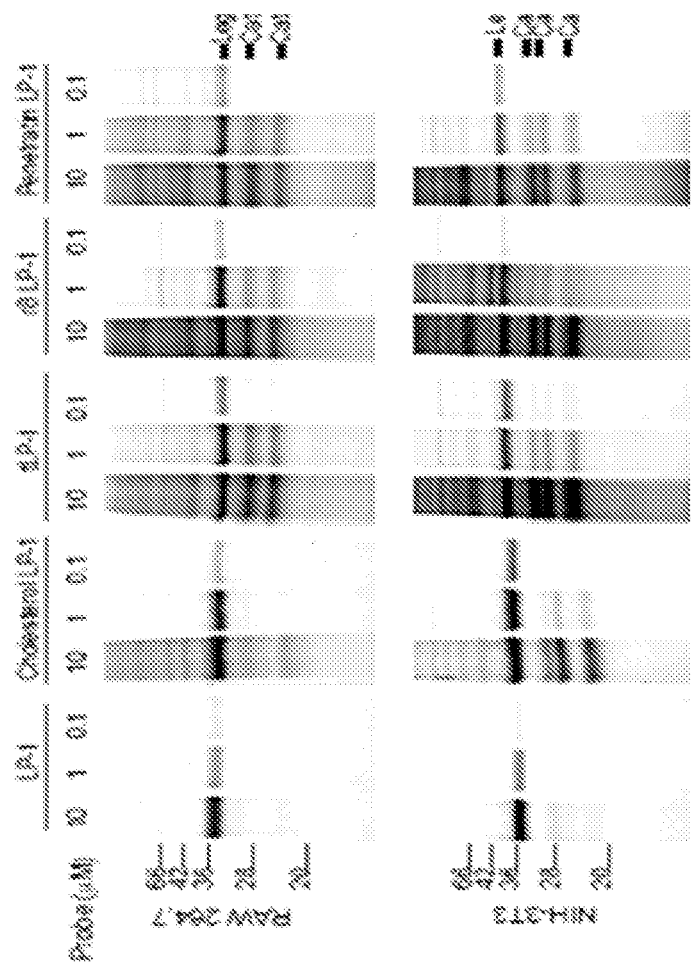

To compare differences in cell permeability and labeling efficiency between these probes, we treated intact cells with each conjugate and analyzed labeling by SDS-PAGE. As previously observed for tLP-I, all the carrier-conjugates showed increased cellular uptake resulting in stronger labeling but also more cross-reactivity (FIG. 12). All CPP conjugated probes, tLP-I, r8 LP-I and penetratin LP-I showed almost identical protein labeling profiles indicating that all of these probes are delivered by similar mechanisms and are enriched in lysosomes. Cholesterol LP-I showed enhanced legumain labeling with less cross-reactivity suggesting that membrane-anchoring cholesterol helped selective delivery of LP-I.

Figure 13:
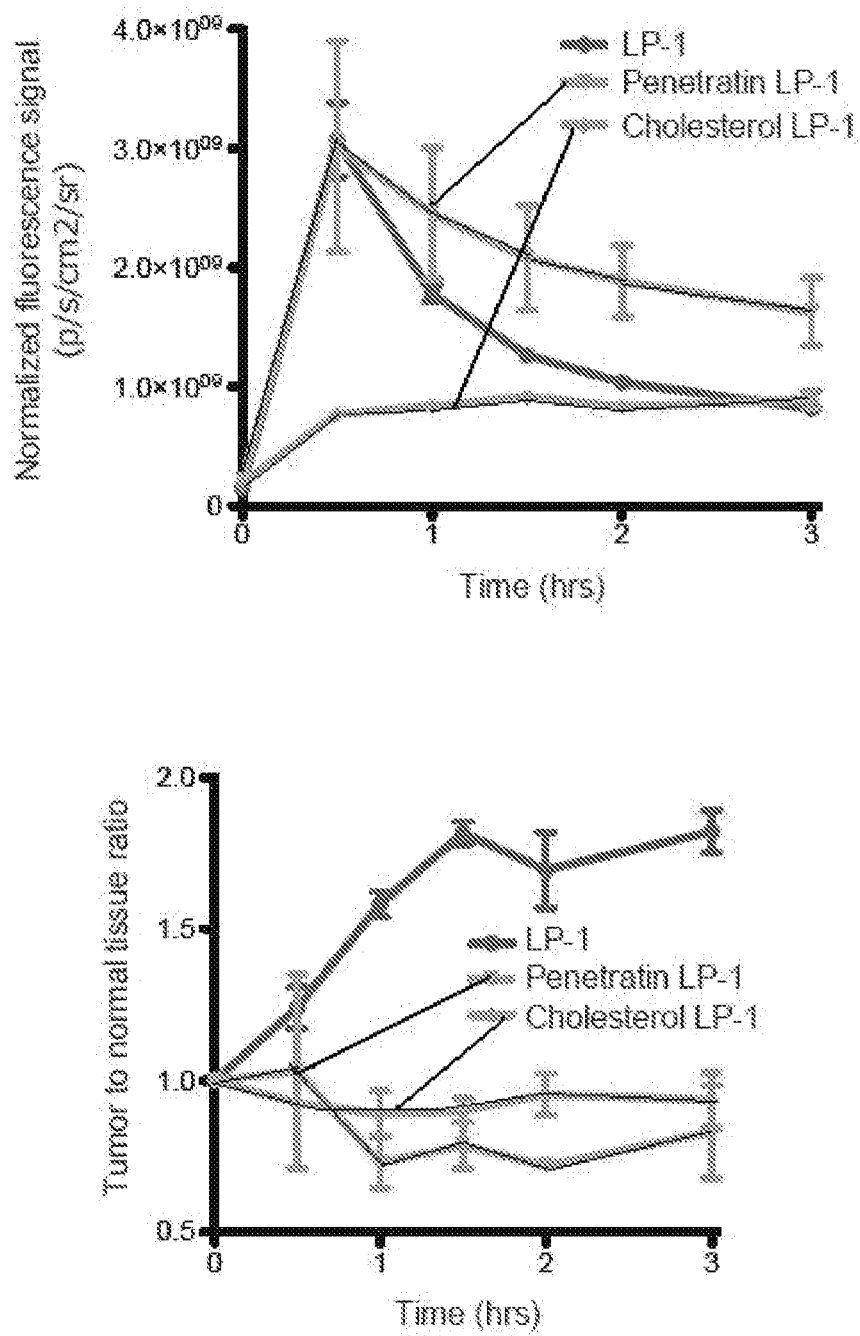
FIG. 13 is a pair of graphs showing normalized fluorescent signal (top) and tissue normalized tissue ratio (bottom) from animals treated with from LP-1 probes that were either unmodified, treated with LP-1 cholesterol, or treated with LP-1 penetratin.

Next, we carried out in vivo imaging experiments with penetratin-LP-I and cholesterol-LP-I to compare their in vivo distribution to LP-I. Photographs were made showing a comparison of in vivo fluorescent images of mice labeled with LP-1 and carrier-conjugated probes (data not shown). Mice bearing C2C12/ras xenograft tumors were IV injected with LP-I or Penetratin LP-I and Cholesterol LP-1 probes and mice imaged at 1 hr, 2 hrs and 3 hrs. Images were analyzed using a colorimetric scale based on photons per second per centimeter square per steradian (p $S^{-1}$ $cm^{-2}$ $sr^{-1}$) overlaid on bright light images. Photographs were also made showing ex vivo imaging of whole organs and SDS-PAGE analysis from the corresponding organ extracts. Fluorescent probe labeled proteins were visualized by scanning of the gel using a flatbed laser scanner. The location of legumain (Leg) is shown. Graphs showing quantification of fluorescent signal in tumors (left) compared to tumor to normal tissue signal ratios (right) are shown in FIG. 13.

Although the carrier labeled probes accumulated in tumors to some extent, their slow clearance resulted in low tumor to background levels Ex vivo imaging of the collected organs followed by analysis of lysates by SDS-PAGE as confirmed that carner labeled probes suffered from increased cross reactivity with cathepsin proteases. Overall, LP-I showed the most legumain labeling in tumors as well as the highest levels of legumain-specific fluorescent signal whereas penetratin LP-I and cholesterol LP-I showed non-specific distribution in most organs and much higher cross reactivity toward cathepsins. We believe that enhanced cellular delivery of these probes adversely affects overall circulation of the probe resulting in less useful imaging reagents. Furthermore, all of the carrier molecules caused increased association with tissues other than the target tumors suggesting that legumain ABPs are more effective as free probes that do not contain a carrier peptide.

The examples below illustrate both an unlabeled and a NIRF-labeled legumain probe, LP-I, which is a highly potent and selective inhibitor. The exemplified probe contains a Pro-Asn-aza epoxide scaffold that is distinct from the previously reported legumain inhibitors. When LP-I was used for non-invasive imaging applications, we were able to monitor legumain activity both in normal tissues and in solid tumors. Its favorable reactivity and clearance resulted in high contrast in tumors rapidly after probe injection. We were also able to track whole body distribution of the probe as well as the level of active legumain in organs by ex vivo imaging and SDS-PAGE. In addition, we tested a series of cell-permeabilizing moieties as a delivery strategy for ABPs. Although some of these moieties improved cell permeability and legumain labeling in cells, they also increased off-target labeling via enhanced lysosomal uptake and extended circulation times in vivo. LP1 and related probes provide a valuable new imaging probe with desirable in vitro and in vivo characteristics. This new imaging agent and its corresponding inhibitor are likely to prove valuable for future in vivo studies of legumain function.

Aza-Michael Acceptor Probe LP-2 and Inhibitor LI-2

A probe having a Cy5 fluorophore and an inhibitor having the same structure without the label and linker were synthesized and tested.

Probes and Inhibitors Having an Asn at P1 and a Normatural Amino Acid at P2 or P3

Figure 17:
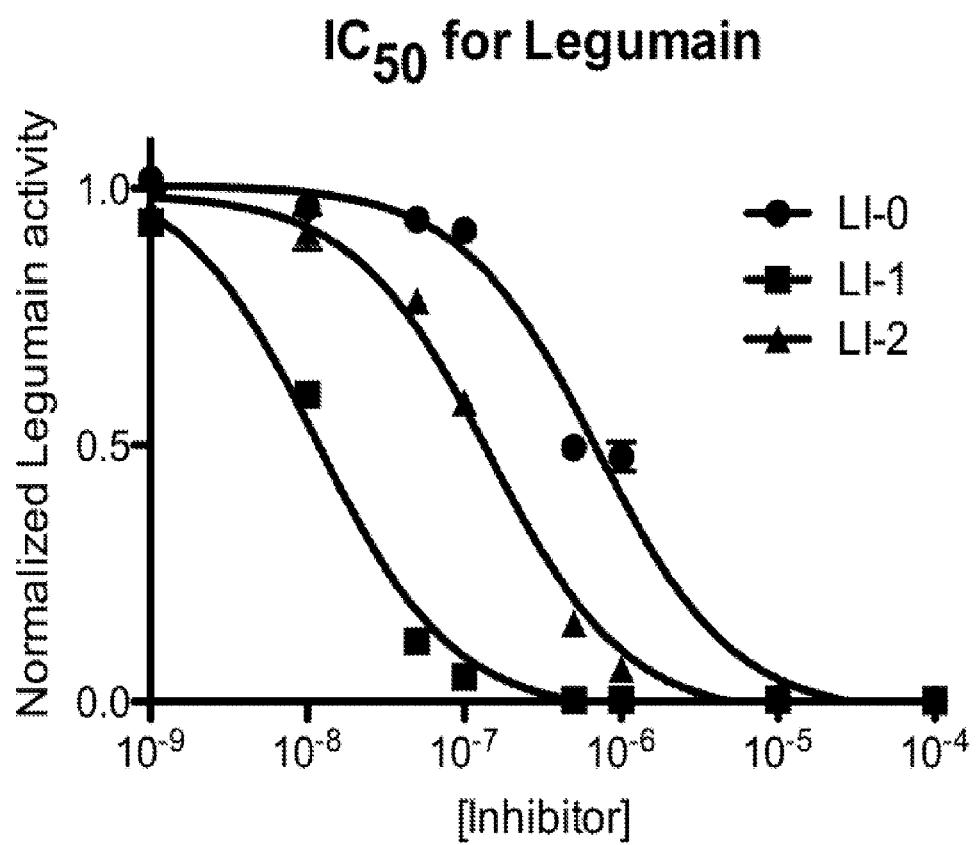
FIG. 17 is a graph showing inhibition of legumain by Li-0, LI-1 and LI-2, and a table giving EC 50 values. "EC" means "IC", or inhibitory concentration.
Figure 18:
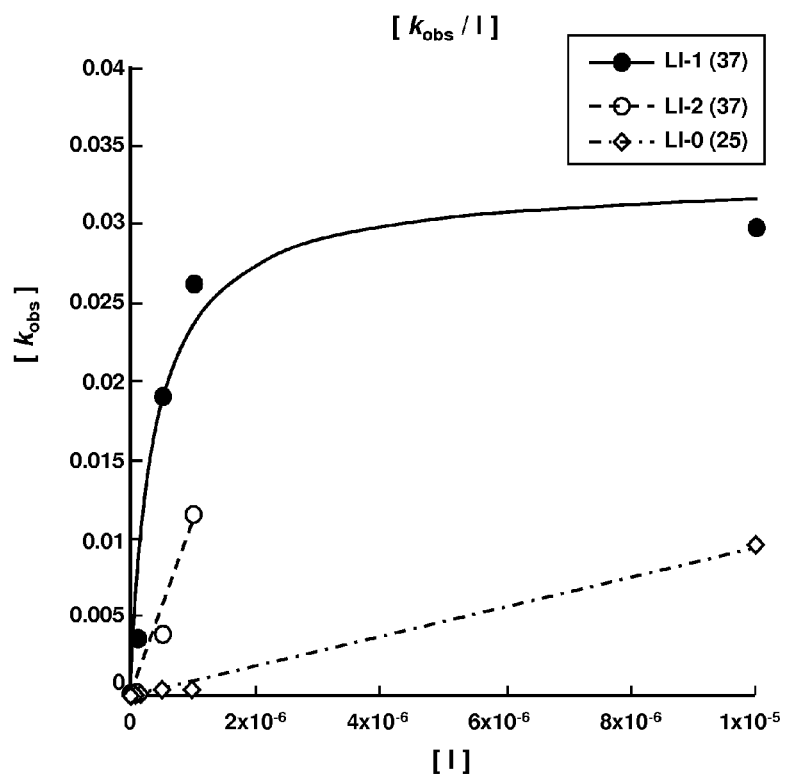
FIG. 18 is a graph of $k_{obs}$ versus inhibitor concentration [I]. Underneath the graph is a table giving values for Li-0(Control), LI-1, LI-2 and controls JPM-Oet and Z-DEVD-FMK. The specificity of LI-1 and LI-2 inhibitors for legumain is shown. Li-1 is shown to have greater potency and rate than either Li-2 or LI-0. Li-2 was the most selective for legumain.
Figure 19:
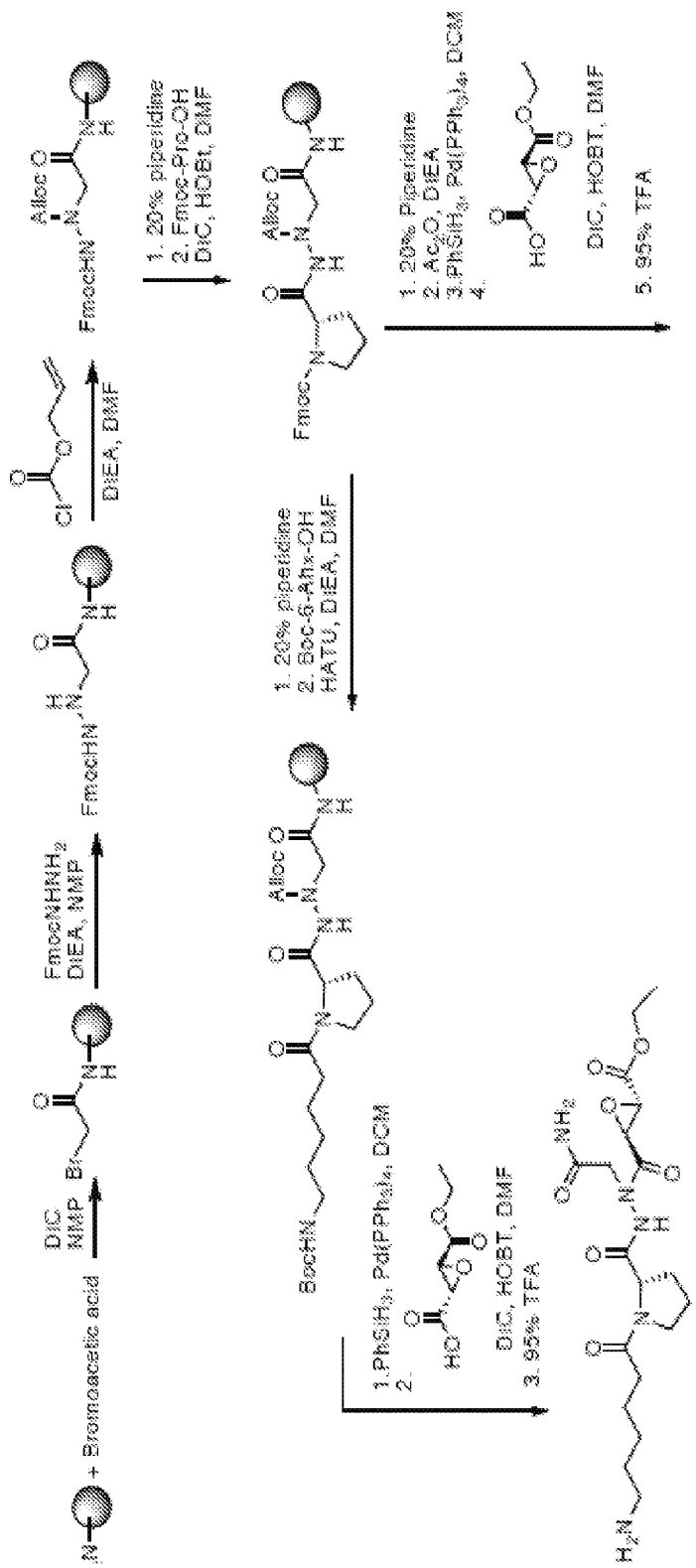
FIG. 19 is a schematic diagram showing the synthesis of the present compounds which have an Aza Michael acceptor warhead. The first four steps are the same as in FIG. 7. Instead of a linker for a label at the R1 position in Formula I, an R group which is a non-natural amino acid is added. R may be varied to include a variety of non-natural amino acids. The illustrated synthesis utilizes proline in P2 and an acetyl capping group.
Figure 20:
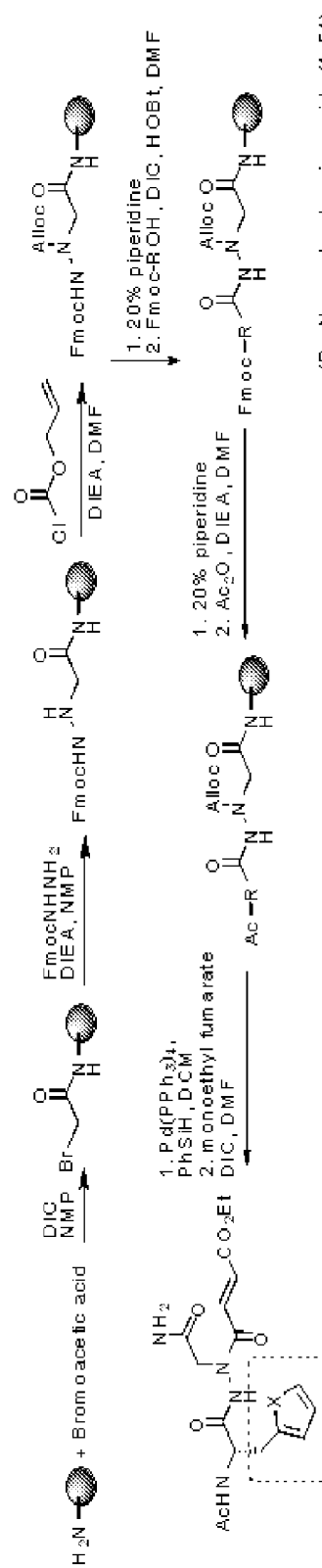
FIG. 20 is a schematic diagram of a reaction scheme for synthesis of a P1-Asn P2-non-natural amino acid legumain inhibitor, having an Aza Michael acceptor warhead, as in the scheme in FIG. 11. Here, the P2 proline employed in FIG. 11 is replaced by a non-natural amino acid, and an acetyl group is used as a capping group; that is, R1 in Formula I would be $CH_2$.
Figure 21:
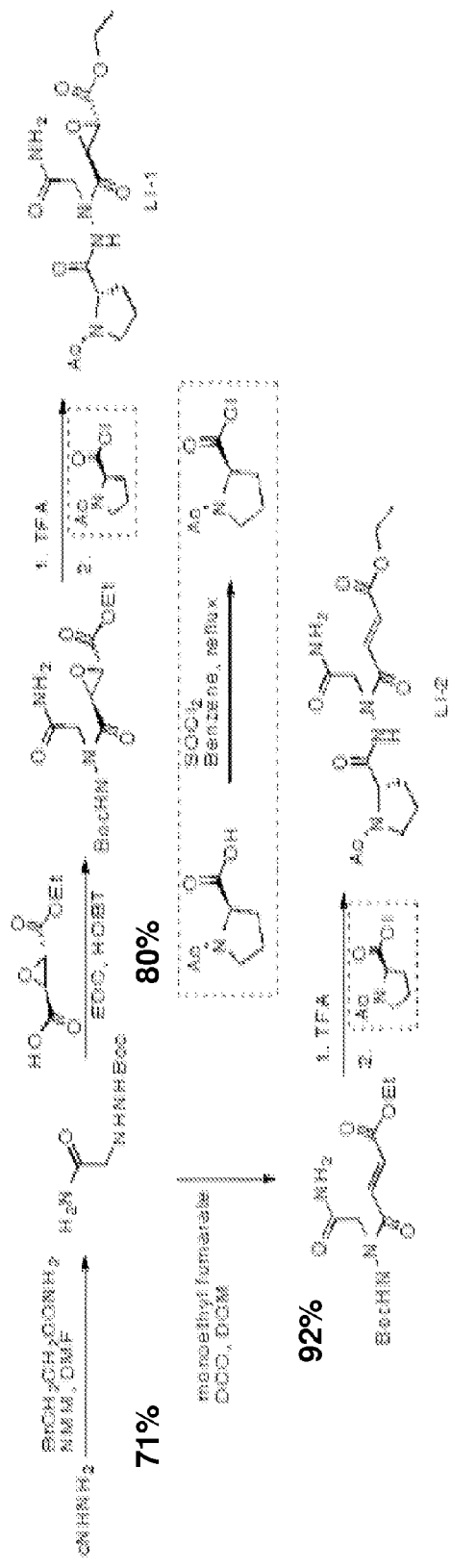
FIG. 21 is a schematic diagram showing a reaction scheme for the synthesis of LI-2 and LI-1. Various R substitutions are possible. This method can be scaled up by conventional solution chemistry.

FIGS. 17 and 18 illustrate embodiments where the inhibitor or probe using an Aza-N Michael acceptor warhead, as in the case of LI-2, is substituted with a non-natural amino acid at the P3 position, where proline is in the P2 position, or substituted with a non-natural amino acid at the P2 position, with no P3 residue.

The table below shows the structures of the amino acids that may be used:

| cmpd # | Amino Acid | Non-Natural Amino Acids Structure |
|---|---|---|
| 1 | (2furyl)alanine | |
| 2 | (2thienyl)alanine | |
| 3 | 4pyridylAla | |
| 4 | 1amino1cyclohexane carboxylic acid | |
| 5 | 1amino1cyclopentane-carboxylic acid | |
| 6 | 2-Abz | |
| 7 | 3Abz | |

-continued
| cmpd # | Amino Acid | Non-Natural Amino Acids Structure |
|---|---|---|
| 8 | 2Abu | 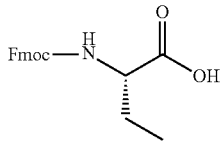 |
| 9 | 3amino3phenylpropionic acid | 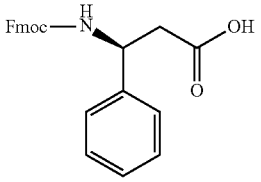 |
| 10 | dehydroAbu | 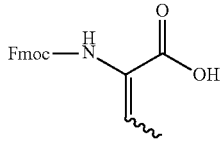 |
| 11 | ACPC | 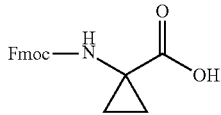 |
| 12 | Aib | 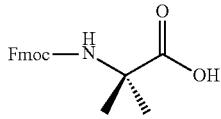 |
| 13 | AllylGly | 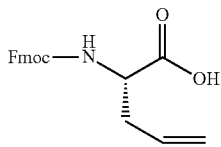 |
| 14 | Amb | 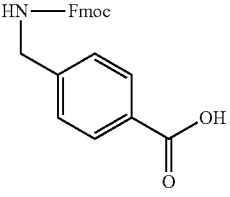 |
| 15 | Amc | 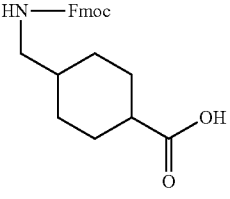 |

-continued
| cmpd # | Amino Acid | Non-Natural Amino Acids Structure |
|---|---|---|
| 16 | Bip | 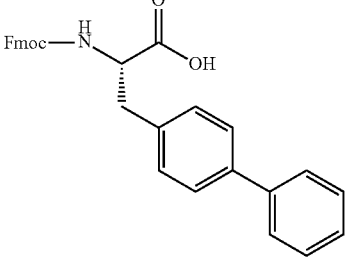 |
| 17 | Bpa | 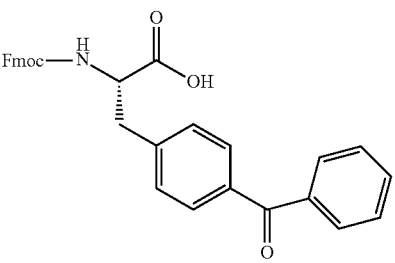 |
| 18 | Cba | 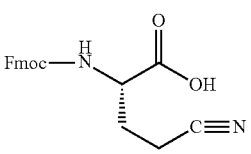 |
| 19 | Cha | 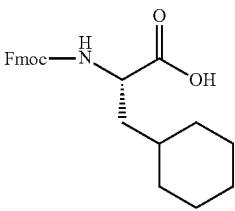 |
| 20 | deltaLeu | 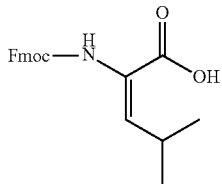 |
| 21 | deltaVal | 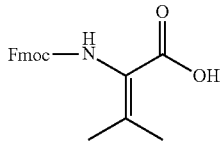 |
| 22 | Hyp | 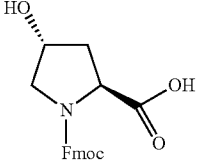 |

-continued

| cmpd # | Amino Acid | Non-Natural Amino Acids Structure |
|---|---|---|
| 23 | Igl | |
| 24 | Inp | |
| 25 | 1-Nal | |
| 26 | 2-Nal | |
| 27 | Nva | |
| 28 | 4-nitroPhe | |
| 29 | 4MethylPhe | |

-continued

| cmpd # | Amino Acid | Non-Natural Amino Acids Structure |
|---|---|---|
| 30 | 4-Methyl-DPhe | |
| 31 | Phe(pI) | |
| 32 | Phe4NH(Boc) | |
| 33 | hPhe | |
| 34 | Phg | |
| 35 | pip | |
| 36 | Dpip | |

-continued

| cmpd # | Amino Acid | Non-Natural Amino Acids Structure |
|---|---|---|
| 37 | propargylglycine | Fmoc-NH-CH(CO-OH)-CH2-C≡CH |
| 38 | Thz | Fmoc-thiazolidine-4-carboxylic acid |
| 39 | Tic | N-Fmoc-1,2,3,4-tetrahydroisoquinoline-3-carboxylic acid |
| 40 | Tle | Fmoc-NH-CH(CO-OH)-C(CH3)3 |
| 41 | 3-NitroTyr | Fmoc-NH-CH(CO-OH)-CH2-(3-NO2-4-OH-C6H3) |
| 42 | leu | Fmoc-NH-CH(CO-OH)-CH2-CH(CH3)2 |
| 43 | Fmoc-L-neopentylglycine | FmocHN-CH(CO2H)-CH2-C(CH3)2-CH=... |
| 44 | Fmoc-pCl-L-Phe-OH | FmocHN-CH(CO2H)-CH2-(4-Cl-C6H4) |

-continued
| cmpd # | Amino Acid | Non-Natural Amino Acids Structure |
|---|---|---|
| 45 | Fmoc-pBr-L-Phe-OH | 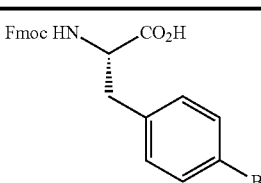 |
| 46 | Fmoc-4-amino-tetrahydropyran-4-carboxylic acid | 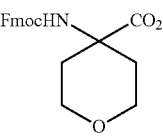 |
| 47 | Fmoc-L-Hol | 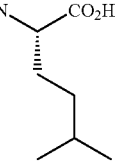 |
| 48 | Fmoc-Pip(Boc)-OH | 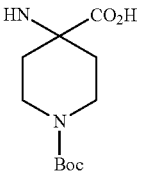 |
| 49 | Fmoc-L-styrylalanine | 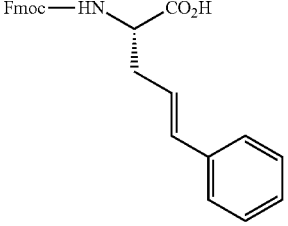 |
| 50 | Fmoc-L-homoCha | 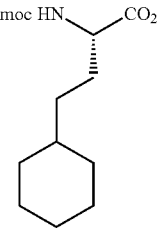 |
| 51 | Fmoc-L-Dab(Boc)-OH | 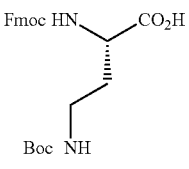 |
| 52 | Fmoc-L-Dapa(Boc)-OH | 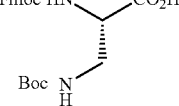 |

-continued

| cmpd # | Amino Acid | Non-Natural Amino Acids Structure |
|---|---|---|
| 53 | Fmoc-4-[2-(Boc-amino)ethoxy]-L-phenylalanine | |
| 54 | Fmoc-4-(tert-butoxycarbonylmethoxy)-L-phenylalanine | |

Amounts of amino acid used are shown in the following Table 3:

| cmpd # | Amino Acid | M= | amount of mmol resin: 0.04 amount of mg |
|---|---|---|---|
| 1 | (2furyl)alanine | 377.13 | 45.256 |
| 2 | (2thienyl)alanine | 393.1 | 47.172 |
| 3 | 4pyridylAla | 388.14 | 46.577 |
| 4 | 1aminolcyclohexane carboxylic acid | 365.42 | 43.85 |
| 5 | 1aminolcyclopentanecarboxylic acid | 351.4 | 42.168 |
| 6 | 2-Abz | 359.4 | 43.128 |
| 7 | 3Abz | 359.38 | 43.126 |
| 8 | 2Abu | 325.35 | 39.042 |
| 9 | 3amino3phenylpropionic acid | | 0 |
| 10 | dehydroAbu | 323.33 | 38.8 |
| 11 | ACPC | 323.33 | 38.8 |
| 12 | Aib | 325.36 | 39.043 |
| 13 | AllylGly | | 0 |
| 14 | Amb | 373.39 | 44.807 |
| 15 | Amc | 379.44 | 45.533 |
| 16 | Bip | 463.53 | 55.624 |
| 17 | Bpa | 491.54 | 58.985 |
| 18 | Cba | 350.36 | 42.043 |
| 19 | Cha | 393.47 | 47.216 |
| 20 | deltaLeu | 351.4 | 42.168 |
| 21 | deltaVal | 337.38 | 40.486 |
| 22 | Hyp | 353.37 | 42.404 |
| 23 | Igl | 413.48 | 49.618 |
| 24 | Inp | 351.38 | 42.166 |
| 25 | 1-Nal | 437.5 | 52.5 |
| 26 | 2-Nal | 437.5 | 52.5 |
| 27 | Nva | 339.38 | 40.726 |
| 28 | 4-nitroPhe | 432.41 | 51.889 |
| 29 | 4MethylPhe | | 0 |
| 30 | 4Methyl-DPhe | 401.46 | 48.175 |
| 31 | Phe(pI) | 513.31 | 61.597 |
| 32 | Phe4NH(Boc) | 502.54 | 60.305 |
| 33 | hPhe | 401.46 | 48.175 |
| 34 | Phg | | 0 |
| 35 | pip | 351.4 | 42.168 |
| 36 | Dpip | 351.4 | 42.168 |
| 37 | propargylglycine | 335.12 | 40.214 |
| 38 | Thz | 355.39 | 42.647 |
| 39 | Tic | 399.45 | 47.934 |
| 40 | Tle | 353.41 | 42.409 |
| 41 | 3-NitroTyr | 448.4 | 53.808 |
| 42 | leu | | 0 |
| 43 | Fmoc-L-neopentylglycine | 367.44 | |
| 44 | Fmoc-pCl-L-Phe-OH | 421.19 | |
| 45 | Fmoc-pBr-L-Phe-OH | 466.34 | |
| 46 | Fmoc-4-amino-tetrahydropyran-4-carboxylic acid | 367.4 | |
| 47 | Fmoc-L-Hol | 367.45 | |
| 48 | Fmoc-Pip(Boc)-OH | 466.53 | |
| 49 | Fmoc-L-styrylalanine | 413.48 | |
| 50 | Fmoc-L-homoCha | 407.52 | |
| 51 | Fmoc-L-Dab(Boc)-OH | 440.5 | |
| 52 | Fmoc-L-Dapa(Boc)-OH | 426.48 | |
| 53 | Fmoc-4-[2-(Boc-amino)ethoxy]-L-phenylalanine | 546.62 | |
| 54 | Fmoc-4-(tert-butoxycarbonylmethoxy)-L-phenylalanine | 517.58 | |

REFERENCES

1. Ishii, S. (1994) Legumain: asparaginyl endopeptidase, *Methods Enzymol* 244, 604-615.
2. Manoury, B., Mazzeo, D., Li, D. N., Billson, J., Loak, K., Benaroch, P., and Watts, C. (2003) Asparagine endopeptidase can initiate the removal of the MHC class II invariant chain chaperone, *Immunity* 18, 489-498.
3. Maehr, R., Hang, H. C., Mintern, J. D., Kim, Y. M., Cuvillier, A., Nishimura, M., Yamada, K., Shirahama-Noda, K., Hara-Nishimura, I., and Ploegh, H. L. (2005) Asparagine endopeptidase is not essential for class II MHC antigen presentation but is required for processing of cathepsin L in mice, *J Immunol* 174, 7066-7074.
4. Morita, Y., Araki, H., Sugimoto, T., Takeuchi, K., Yamane, T., Maeda, T., Yamamoto, Y., Nishi, K., Asano, M., Shirahama-Noda, K., Nishimura, M., Uzu, T., Hara-Nishimura, I., Koya, D., Kashiwagi, A., and Ohkubo, I. (2007) Legumain/asparaginyl endopeptidase controls extracellular matrix remodeling through the degradation of fibronectin in mouse renal proximal tubular cells, *FEBS Lett* 581, 1417-1424.
5. Sottile, J., and Hocking, D. C. (2002) Fibronectin polymerization regulates the composition and stability of extracellular matrix fibrils and cell-matrix adhesions, *Mol Biol Cell* 13, 3546-3559.

6. Gotz, M. G., James, K. E., Hansell, E., Dvorak, J., Seshaadri, A., Sojka, D., Kopacek, P., McKerrow, J. H., Caffrey, C. R., and Powers, J. C. (2008) Aza-peptidyl Michael acceptors. A new class of potent and selective inhibitors of asparaginyl endopeptidases (legumains) from evolutionarily diverse pathogens, *J Med Chem* 51, 2816-2832.

7. James, K. E., Gotz, M. G., Caffrey, C. R., Hansell, E., Carter, W., Barrett, A. J., McKerrow, J. H., and Powers, J. C. (2003) Aza-peptide epoxides: potent and selective inhibitors of *Schistosoma mansoni* and pig kidney legumains (asparaginyl endopeptidases), *Biol Chem* 384, 1613-1618.

8. Clerin, V., Shih, H. H., Deng, N., Hebert, G., Resmini, C., Shields, K. M., Feldman, J. L., Winkler, A., Albert, L., Maganti, V., Wong, A., Paulsen, J. E., Keith, J. C., Jr., Vlasuk, G. P., and Pittman, D. D. (2008) Expression of the cysteine protease legumain in vascular lesions and functional implications in atherogenesis, *Atherosclerosis* 201, 53-66.

9. Liu, C., Sun, C., Huang, H., Janda, K., and Edgington, T. (2003) Overexpression of legumain in tumors is significant for invasion/metastasis and a candidate enzymatic target for prodrug therapy, *Cancer Res* 63, 2957-2964.

10. Luo, Y., Zhou, H., Krueger, J., Kaplan, C., Lee, S. H., Dolman, C., Markowitz, D., Wu, W., Liu, C., Reisfeld, R. A., and Xiang, R. (2006) Targeting tumor-associated macrophages as a novel strategy against breast cancer, *J Clin Invest* 116, 2132-2141.

11. Chan, C. B., Abe, M., Hashimoto, N., Hao, C., Williams, I. R., Liu, X., Nakao, S., Yamamoto, A., Zheng, C., Henter, J. I., Meeths, M., Nordenskjold, M., Li, S. Y., Hara-Nishimura, I., Asano, M., and Ye, K. (2009) Mice lacking asparaginyl endopeptidase develop disorders resembling hemophagocytic syndrome, *Proc Natl Acad Sci USA* 106, 468-473.

12. Kembhavi, A. A., Buttle, D. J., Knight, C. G., and Barrett, A. J. (1993) The two cysteine endopeptidases of legume seeds: purification and characterization by use of specific fluorometric assays, *Arch Biochem Biophys* 303, 208-213.

13. Niestroj, A. J., Feussner, K., Heiser, U., Dando, P. M., Barrett, A., Gerhartz, B., and Demuth, H. U. (2002) Inhibition of mammalian legumain by Michael acceptors and AzaAsn-halomethylketones, *Biol Chem* 383, 1205-1214.

14. Sexton, K. B., Witte, M. D., Blum, G., and Bogyo, M. (2007) Design of cell-permeable, fluorescent activity-based probes for the lysosomal cysteine protease asparaginyl endopeptidase (AEP)/legumain, *Bioorg Med Chem Lett* 17, 649-653.

15. Kato, D., Boatright, K. M., Berger, A. B., Nazif, T., Blum, G., Ryan, C., Chehade, K. A., Salvesen, G. S., and Bogyo, M. (2005) Activity-based probes that target diverse cysteine protease families, *Nat Chem Biol* 1, 33-38.

16. Rozman-Pungercar, J., Kopitar-Jerala, N., Bogyo, M., Turk, D., Vasiljeva, O., Stefe, I., Vandenabeele, P., Bromme, D., Puizdar, V., Fonovic, M., Trstenjak-Prebanda, M., Dolenc, I., Turk, V., and Turk, B. (2003) Inhibition of papain-like cysteine proteases and legumain by caspase-specific inhibitors: when reaction mechanism is more important than specificity, *Cell Death Differ* 10, 881-888.

17. Loak, K., Li, D. N., Manoury, B., Billson, J., Morton, F., Hewitt, E., and Watts, C. (2003) Novel cell-permeable acyloxymethylketone inhibitors of asparaginyl endopeptidase, *Biol Chem* 384, 1239-1246.

18. Edgington, L. E., Berger, A. B., Blum, G., Albrow, V. E., Paulick, M. G., Lineberry, N., and Bogyo, M. (2009) Noninvasive optical imaging of apoptosis by caspase-targeted activity-based probes, *Nat Med* 15, 967-973.

19. Berger, A. B., Witte, M. D., Denault, J. B., Sadaghiani, A. M., Sexton, K. M., Salvesen, G. S., and Bogyo, M. (2006) Identification of early intermediates of caspase activation using selective inhibitors and activity-based probes, *Mol Cell* 23, 509-521.

20. Kato, D., Verhelst, S. H., Sexton, K. B., and Bogyo, M. (2005) A general solid phase method for the preparation of diverse azapeptide probes directed against cysteine proteases, *Org Lett* 7, 5649-5652.

21. Joyce, J. A., Baruch, A., Chehade, K., Meyer-Morse, N., Giraudo, E., Tsai, F. Y., Greenbaum, D. C., Hager, J. H., Bogyo, M., and Hanahan, D. (2004) Cathepsin cysteine proteases are effectors of invasive growth and angiogenesis during multistage tumorigenesis, *Cancer Cell* 5, 443-453.

22. Asgian, J. L., James, K. E., Li, Z. Z., Carter, W., Barrett, A. J., Mikolajczyk, J., Salvesen, G. S., and Powers, J. C. (2002) Aza-peptide epoxides: a new class of inhibitors selective for clan CD cysteine proteases, *J Med Chem* 45, 4958-4960.

23. Shirahama-Noda, K., Yamamoto, A., Sugihara, K., Hashimoto, N., Asano, M., Nishimura, M., and Hara-Nishimura, I. (2003) Biosynthetic processing of cathepsins and lysosomal degradation are abolished in asparaginyl endopeptidase-deficient mice, *J Biol Chem* 278, 33194-33199.

24. Blum, G., von Degenfeld, G., Merchant, M. J., Blau, H. M., and Bogyo, M. (2007) Noninvasive optical imaging of cysteine protease activity using fluorescently quenched activity-based probes, *Nat Chem Biol* 3, 668-677.

25. Lennon-Dumenil, A. M., Bakker, A. H., Maehr, R., Fiebiger, E., Overkleeft, H. S., Rosemblatt, M., Ploegh, H. L., and Lagaudriere-Gesbert, C. (2002) Analysis of protease activity in live antigen-presenting cells shows regulation of the phagosomal proteolytic contents during dendritic cell activation, *J Exp Med* 196, 529-540.

26. Fischer, R., Fotin-Mleczek, M., Hufnagel, H., and Brock, R. (2005) Break on through to the other side-biophysics and cell biology shed light on cell-penetrating peptides, *Chembiochem* 6, 2126-2142.

27. Mintzer, M. A., and Simanek, E. E. (2009) Nonviral vectors for gene delivery, *Chem Rev* 109, 259-302.

28. Rajendran, L., Schneider, A., Schlechtingen, G., Weidlich, S., Ries, J., Braxmeier, T., Schwille, P., Schulz, J. B., Schroeder, C., Simons, M., Jennings, G., Knolker, H. J., and Simons, K. (2008) Efficient inhibition of the Alzheimer's disease beta-secretase by membrane targeting, *Science* 320, 520-523.

29. Sexton, K. B., Kato, D., Berger, A. B., Fonovic, M., Verhelst, S. H., and Bogyo, M. (2007) Specificity of aza-peptide electrophile activity-based probes of caspases, *Cell Death Differ* 14, 727-732.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, and are incorporated for the purpose of further describing and enabling the method or material referred to.

What is claimed is:

1. A compound, having a formula according to either Formula I or Formula II below

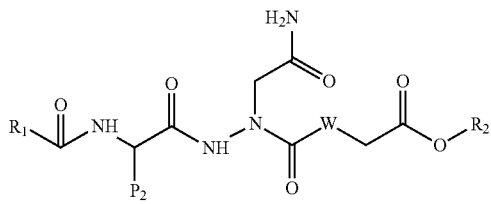

Formula I

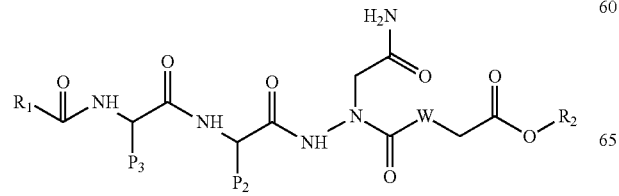

Formula II wherein, (a) R1 is either (i) linker-label, wherein linker is lower alkyl, lower alkyl-aryl, or aryl; and label is a radiolabel or an optical label, said linker optionally comprising a cell penetrating peptide; or (ii) lower alkyl, lower alkyl-aryl, or aryl without a label;

(b) P3 is a side chain of leucine or a non-natural amino-acid selected from the group consisting of (2-furyl)alanine, (2-thienyl)alanine, 4-pyridylAla, 1-amino-1-cyclohexane carboxylic acid, 1-amino-1-cyclopentane carboxylic acid, 2-Abz, 3-Abz-, 2-Abu, 3-amino-3-phenyl propionic acid, dehydroAbu, ACPC, Aib, AllylGly, Amb, Amc, Bip, Bpa, Cba, Cha, deltaLeu, deltaVal, Hyp, Igl, Inp, 1-Nal, 2-Nal, Nva, 4-nitroPhe, 4-MethylPhe, 4-Methyl-D Phe, Phe(pI), Phe-4-NH(Boc), hPhe, Phg, pip, Dpip, propargylglycine, Thz, Tic, Tle, 3-NitroTyr, Fmoc-L-neopentylglycine, Fmoc-pCl-L-Phe-OH, Fmoc-pBr-L-Phe-OH, Fmoc-4-amino-tetrahydropyran-4-carboxylic acid, Fmoc-L-Hol, Fmoc-Pip(Boc)-OH, Fmoc-L-styrylalanine, Fmoc-L-homoCha, Fmoc-L-Dab(Boc)-OH, Fmoc-L-Dapa(Boc)-OH, Fmoc-4-[2-(Boc-amino)ethoxy]-L-phenylalanine, and Fmoc-4-(tert-butoxycarbonylmethoxy)-L-phenylalanine;

(c) P2 is selected from the group consisting of (i) proline such that the compound of Formula I is

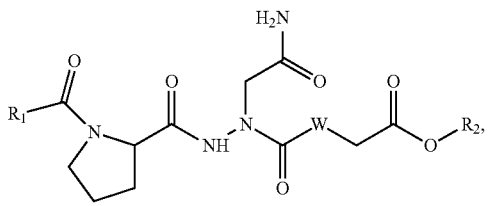

(ii) a side chain of leucine, and (iii) a side chain of a non-natural amino acid as defined for P3;
(d) W has the formula of a C double bonded to its adjacent CH group or an epoxide group wherein W is C and an epoxide oxygen is bonded to it and an adjacent carbon; and
(e) R2 is selected from the group consisting of lower alkyl, aryl, and lower alkyl-aryl.

2. A compound of claim 1 having the formula,

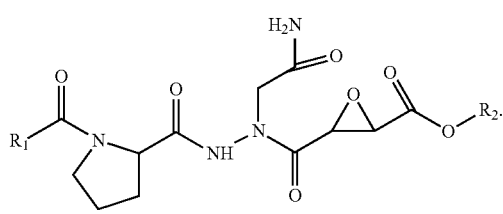

3. A compound of claim 1 or 2 wherein R1 is lower alkyl linked to a fluorescent dye.

4. A compound of claim 3 wherein the fluorescent dye is Cy5.

5. A compound of claim 2 wherein R1 is linked to a dye and R2 is ethyl.

6. A compound of claim 1 wherein R1 is linked to a dye and R2 is ethyl.

7. A compound of claim 1 according to formula I wherein W is a double bond and P2 is proline.

8. A compound according to one of claim 1, 2, 5 or 6 wherein R2 is ethyl, methyl, propyl or butyl.

9. A method of inhibiting legumain activity, comprising the step of contacting the legumain with a compound as defined in claim 1.

10. A method according to claim 9 wherein R1 is a lower alkyl or aryl group without a label.

11. A method according to claim 9 wherein the compound is a compound having the formula:

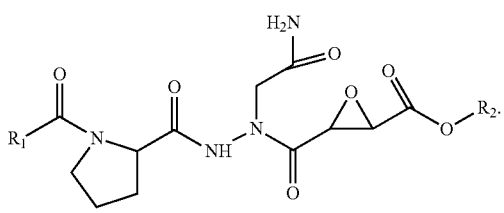

12. A method according to claim 9 wherein the compound is a compound having the formula:

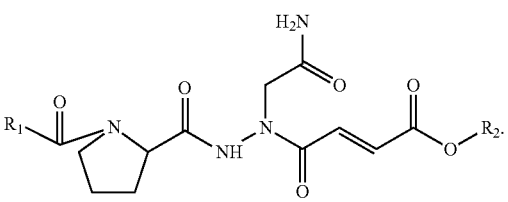

13. A method according to claim 12 wherein R1 and R2 are independently a lower alkyl linker having between three and twelve atoms linked to a label.

14. A method according to claim 13 wherein R1 comprises a cell penetrating peptide.

15. A method according to claim 14 wherein R2 is ethyl, methyl, propyl or butyl.

16. A method of imaging a tissue in an organism having active legumain in the tissue, comprising
    administering to the organism a compound according to claim 1 wherein R1 is linker-label wherein linker is lower alkyl, lower alkyl-aryl, or aryl; and label is a radiolabel or an optical label, said linker optionally comprising a cell penetrating peptide; and
    imaging the tissue of the organism.

17. A method according to claim 16 wherein R1 is a linker to a fluorescent dye.

18. A method according to claim 16 wherein said tissue is a tumor labeled by said compound.

19. A pharmaceutical composition comprising a compound according to claim 1 and an excipient or carrier.

20. The compound of claim 1, wherein said linker further comprises a cell penetrating peptide selected from the group consisting of a Tat peptide, an arginine-rich permeation peptide sequence based on a Tat peptide, octa-arginine, and penetratin.

21. The compound of claim 20, wherein the cell penetrating peptide is a Tat peptide.

22. A compound according to claim 4, wherein R2 is ethyl, methyl, propyl or butyl.

* * * * *

SEQUENCE LISTING

<160> NUMBER OF SEQ ID NOS: 14

<210> SEQ ID NO 1
<211> LENGTH: 11
<212> TYPE: PRT
<213> ORGANISM: artificial
<220> FEATURE:
<223> OTHER INFORMATION: synthetic

<400> SEQUENCE: 1

Ala Cys Arg Arg Arg Arg Arg Arg Arg Arg Cys
1               5                   10

<210> SEQ ID NO 2
<211> LENGTH: 17
<212> TYPE: PRT
<213> ORGANISM: Artificial
<220> FEATURE:
<223> OTHER INFORMATION: synthetic

<400> SEQUENCE: 2

Arg Gln Ile Lys Ile Trp Phe Gln Asn Arg Arg Met Lys Trp Lys Lys
1               5                   10                  15

Cys

<210> SEQ ID NO 3
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: natural amino acid
<222> LOCATION: (6)..(6)
<223> OTHER INFORMATION: ornithine

<400> SEQUENCE: 3

Arg Lys Lys Arg Arg Xaa Arg Arg Cys
1               5

<210> SEQ ID NO 4
<211> LENGTH: 16
<212> TYPE: PRT
<213> ORGANISM: Artificial
<220> FEATURE:
<223> OTHER INFORMATION: synthetic

<400> SEQUENCE: 4

Arg Gln Ala Arg Arg Asn Arg Arg Arg Trp Arg Glu Arg Gln Arg
1               5                   10                  15

<210> SEQ ID NO 5
<211> LENGTH: 19
<212> TYPE: PRT
<213> ORGANISM: Artificial
<220> FEATURE:
<223> OTHER INFORMATION: synthetic

<400> SEQUENCE: 5

Met Pro Lys Thr Arg Arg Arg Pro Arg Arg Ser Gln Arg Lys Arg Pro
1               5                   10                  15

Pro Thr Pro

<210> SEQ ID NO 6
<211> LENGTH: 30
<212> TYPE: PRT

```
<213> ORGANISM: Artificial
<220> FEATURE:
<223> OTHER INFORMATION: Synthetic

<400> SEQUENCE: 6

Val Ala Tyr Ile Ser Arg Gly Gly Val Ser Thr Tyr Tyr Ser Asp Thr
1               5                   10                  15
Val Lys Gly Arg Phe Thr Arg Gln Lys Tyr Asn Lys Arg Ala
            20                  25                  30

<210> SEQ ID NO 7
<211> LENGTH: 9
<212> TYPE: PRT
<213> ORGANISM: Artificial
<220> FEATURE:
<223> OTHER INFORMATION: synthetic

<400> SEQUENCE: 7

Arg Lys Lys Arg Arg Asn Arg Arg Arg
1               5

<210> SEQ ID NO 8
<211> LENGTH: 15
<212> TYPE: PRT
<213> ORGANISM: Artificial
<220> FEATURE:
<223> OTHER INFORMATION: synthetic
<220> FEATURE:
<221> NAME/KEY: non natural amino acid
<222> LOCATION: (6)..(7)
<220> FEATURE:
<221> NAME/KEY: non natural amino acid
<222> LOCATION: (6)..(7)
<223> OTHER INFORMATION: x is ornithine

<400> SEQUENCE: 8

Arg Lys Lys Arg Arg Xaa Arg Arg Arg Ala His Ala Lys Gly Cys
1               5                   10                  15

<210> SEQ ID NO 9
<211> LENGTH: 15
<212> TYPE: PRT
<213> ORGANISM: artificial
<220> FEATURE:
<223> OTHER INFORMATION: synthetic

<400> SEQUENCE: 9

Arg Lys Lys Arg Arg Glu Arg Arg Arg Ala His Ala Lys Gly Cys
1               5                   10                  15

<210> SEQ ID NO 10
<211> LENGTH: 26
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: X is norleucine

<400> SEQUENCE: 10

Arg Lys Lys Arg Arg Xaa Arg Arg Arg Ala His Ala Lys Gly Cys Ala
1               5                   10                  15
Cys Arg Arg Arg Arg Arg Arg Arg Arg Cys
            20                  25
```

```
<210> SEQ ID NO 11
<211> LENGTH: 16
<212> TYPE: PRT
<213> ORGANISM: Artificial
<220> FEATURE:
<223> OTHER INFORMATION: synthetic

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 9
<212> TYPE: PRT
<213> ORGANISM: Artificial
<220> FEATURE:
<223> OTHER INFORMATION: synthetic

<400> SEQUENCE: 12

Arg Arg Arg Arg Arg Arg Arg Arg Arg
1               5

<210> SEQ ID NO 13
<211> LENGTH: 9
<212> TYPE: PRT
<213> ORGANISM: Artificial
<220> FEATURE:
<223> OTHER INFORMATION: synthetic

<400> SEQUENCE: 13

Arg Ala Ala Arg Arg Ala Ala Arg Arg
1               5

<210> SEQ ID NO 14
<211> LENGTH: 12
<212> TYPE: PRT
<213> ORGANISM: Artificial
<220> FEATURE:
<223> OTHER INFORMATION: synthetic

<400> SEQUENCE: 14

Pro Leu Ser Ser Ile Phe Ser Arg Ile Gly Asp Pro
1               5                   10
```